US012636081B2

(12) United States Patent
Blau et al.

(10) Patent No.: US 12,636,081 B2
(45) Date of Patent: May 26, 2026

(54) ARTIFICIAL-INTELLIGENCE-BASED DETERMINATION OF IMPLANTATION CURVE

(71) Applicant: metamorphosis GmbH, Altenbeken (DE)

(72) Inventors: Arno Blau, Staufen (DE); Artur Lamm, Staufen (DE); Aaron Pries, Staufen (DE)

(73) Assignee: Metamorphosis GmbH (DE)

( * ) Notice: Subject to any disclaimer, the term of this patent is extended or adjusted under 35 U.S.C. 154(b) by 405 days.

(21) Appl. No.: 18/258,031

(22) PCT Filed: Dec. 17, 2021

(86) PCT No.: PCT/EP2021/086538
§ 371 (c)(1),
(2) Date: Jun. 16, 2023

(87) PCT Pub. No.: WO2022/136169
PCT Pub. Date: Jun. 30, 2022

(65) Prior Publication Data
US 2024/0099775 A1     Mar. 28, 2024

(30) Foreign Application Priority Data

Dec. 21, 2020    (EP) ..................................... 20216188

(51) Int. Cl.
| | |
|---|---|
| *A61B 34/10* | (2016.01) |
| *A61B 17/72* | (2006.01) |
| *A61B 90/00* | (2016.01) |

(52) U.S. Cl.
CPC .............. *A61B 34/10* (2016.02); *A61B 17/72* (2013.01); *A61B 90/37* (2016.02);
(Continued)

(58) Field of Classification Search
CPC ... A61B 34/10; A61B 90/37; A61B 2034/105; A61B 2034/107; A61B 2090/367; A61B 2090/376; A61B 17/72–7291
See application file for complete search history.

(56) References Cited

U.S. PATENT DOCUMENTS

| | | | |
|---|---|---|---|
| 5,799,055 A | 8/1998 | Peshkin | |
| 6,477,400 B1 | 11/2002 | Barrick | |
(Continued)

FOREIGN PATENT DOCUMENTS

| | | |
|---|---|---|
| EP | 2667352 A1 | 11/2013 |
| EP | 3479790 A2 | 5/2019 |
(Continued)

*Primary Examiner* — Nicholas J Plionis
(74) *Attorney, Agent, or Firm* — LNK LAW, PLLC

(57) ABSTRACT

Systems and methods are provided for determining an implantation curve or path, along which an implant such as a nail or a screw may be inserted and implanted into a bone, and/or to determine an entry point, which is the point at which the surgeon opens the bone for inserting the implant. According to the invention, a 2D X-ray image is received, which X-ray image shows a surgical region of interest. In that X-ray image, a first point associated with a structure of interest as well as an implantation path within the bone for an implant intended to be implanted may be determined. An entry point for an insertion of the implant into the bone is located on the implantation path. It is noted that the first point may not be the entry point.

14 Claims, 36 Drawing Sheets

(52) U.S. Cl.

CPC ... *A61B 2034/105* (2016.02); *A61B 2034/107* (2016.02); *A61B 2090/367* (2016.02); *A61B 2090/376* (2016.02)

(56) References Cited

U.S. PATENT DOCUMENTS

| | | | |
|---|---|---|---|
| 8,165,659 B2 | 4/2012 | Sheffer et al. | |
| 10,499,961 B2 | 12/2019 | Simon et al. | |
| 11,883,118 B2 | 1/2024 | Samadani et al. | |
| 2008/0255442 A1* | 10/2008 | Ashby | A61B 90/36 |
| | | | 600/407 |
| 2008/0287950 A1* | 11/2008 | Frigg | A61B 17/1717 |
| | | | 606/62 |
| 2011/0019884 A1 | 1/2011 | Blau | |
| 2011/0082367 A1 | 4/2011 | Regazzoni | |
| 2011/0201915 A1 | 8/2011 | Gogin et al. | |
| 2015/0140535 A1* | 5/2015 | Geri | G16H 50/50 |
| | | | 434/262 |
| 2016/0157751 A1 | 6/2016 | Mahfouz | |
| 2016/0354156 A1 | 12/2016 | Blau et al. | |
| 2017/0116729 A1 | 4/2017 | Stolka et al. | |
| 2023/0334659 A1 | 10/2023 | Kuo et al. | |

FOREIGN PATENT DOCUMENTS

| | | | |
|---|---|---|---|
| JP | 2010535051 A | 11/2010 | |
| JP | 2013526377 A | 6/2013 | |
| JP | 2013533765 A | 8/2013 | |
| LU | 101009 B1 | 5/2020 | |
| WO | 2009087214 A1 | 7/2009 | |
| WO | 2020056086 A1 | 3/2020 | |
| WO | 2020108806 A1 | 6/2020 | |

* cited by examiner

ARTIFICIAL-INTELLIGENCE-BASED DETERMINATION OF IMPLANTATION CURVE

CROSS-REFERENCE TO RELATED APPLICATION

This application is a U.S. National-Stage entry under 35 U.S.C. § 371 based on International Application No. PCT/EP2021/086538, filed Dec. 17, 2021 which was published under PCT Article 21(2) and which claims priority to EPO Application No. 20216188.1, filed Dec. 21, 2020, which are all hereby incorporated herein in their entirety by reference.

FIELD OF INVENTION

This disclosure pertains to the fields of artificial intelligence and computer assisted surgery. Further, the invention relates to systems and methods providing information related to objects based on X-ray images. In particular, the invention relates to systems and methods for determining an implantation curve and an entry point at a bone. The methods may be implemented as a computer program executable on a processing unit of the systems.

BACKGROUND OF THE INVENTION

In a case in which a long bone is fractured, the pieces of the bone may be stabilized by an implant like an intramedullary nail, which may be inserted into the medullary canal of the bone, or a bone plate, which may be affixed to the surface of the bone, as support for the healing of the fracture. The surgical procedure for implanting such implants may be minimally invasive and may require repeated acquisition of X-ray images to enable the surgeon to correctly place the implant. The implant may also be connected to one or more sub-implants, e.g., a screw or a blade.

There are various critical and difficult steps of an intramedullary nailing procedure of a long bone, including a sufficiently correct reduction of a fracture (ensuring the correct positioning of bone fragments), determining an entry point for inserting the implant into a medullary canal of the bone, and locking of the implant by inserting a screw through a hole in the implant.

A critical step for the implantation of a nail into a long bone is the determination of the entry point. A suboptimal choice for an entry point may lead to non-optimal positioning of the nail and hence also to an unsuitable position of connected sub-implants such as a neck screw or blade. Moreover, if, for a given entry point, the surgeon has already performed reaming, the canal within which the nail will be positioned has been defined and may no longer be corrected.

There are two principal methods of determining an entry point: by palpating or based on X-rays. When palpating, after performing an initial cut, the surgeon feels with a finger the region of the entry point (for instance, in the case of implanting a cephalomedullary nail in the femur, this is the tip of the greater trochanter) and determines the location of the entry point based on the suspected bone surface and a rule of thumb (e.g., the so-called ⅓-⅔-rule). A disadvantage of such a procedure is that by feeling, the bone surface may be determined only imperfectly, which may lead to a substantial deviation from the optimal entry point. Moreover, rules of thumb (e.g., the ⅓-⅔-rule) may be rather suboptimal, depending on the particular anatomy of the patient.

An entry point may also be determined based on X-rays. In case of implanting a cephalomedullary nail into the femur, an anterior-posterior (AP) X-ray image may first be acquired, in which an opening instrument is placed on the tip of the trochanter. Then, a lateral X-ray image is acquired such that the femur shaft and neck are parallel. The tip of the opening instrument is moved in dorsal or ventral direction until the tip is placed in the middle between the two axes (which is checked by X-ray images). Disadvantages of this procedure are that, firstly, acquiring the lateral X-ray image from the right direction is difficult, and secondly, determining the two axes based on X-ray images may only be done imprecisely.

Minimally invasively determining an entry point for inserting a nail into a humerus is even more difficult because a correct reduction of a fracture in the vicinity of neck and head is typically performed while inserting the implant. A correct entry point lies approximately on the most proximal point of the anatomical neck (collum anatomicum), or at a defined distance in medial direction from this point. With a correct reduction of any fracture, the entry point is visible in a perfect anterior-posterior (AP) X-ray image because the most proximal point of the joint outline may be identified in such an image. However, ensuring the correct AP imaging direction is difficult and may even be impossible depending on the physical setup of patient and X-ray imaging device in the operation room (OR). Moreover, even in a perfect AP imaging direction, there is a substantial uncertainty in determining the entry point's position with respect to imaging depth. Acquiring an image from a different viewing direction (e.g., axial direction) may not solve this problem because the entry point may not be identifiable in such an X-ray image.

Even the combination of the two methods for determining an entry point (palpating and acquisition of X-rays) may not generally improve accuracy sufficiently. So far, there is no established computer-assisted surgery (CAS) technique for this problem.

Another challenge in any osteosynthesis procedure is that a sufficiently correct reduction of a fracture is essential for a satisfactory clinical outcome. Typically, fractures heal satisfactorily only if the reduction was correctly performed. Reductions of long bones in particular are often difficult to evaluate during minimally invasive surgery, especially concerning a correct angle of anteversion (in the case of a femur) or angle of torsion (in the case of a humerus or tibia). An incorrect angle of anteversion or torsion is often noticed only after completed surgery. At this stage, an incorrect angle of anteversion or torsion causes major discomfort and restrictions to the patient, even if the fracture itself has healed. Thus, a sufficiently correct angle of anteversion or torsion is essential for a satisfactory clinical outcome, especially for osteosynthesis of the femur, tibia, or humerus. Similar comments apply to the caput-collum-diaphysis (CCD) angle and leg length, which are also critical for satisfactory clinical outcomes.

Malrotation of bone fragments is one of the most common reasons for revision surgeries when treating fractures of tibia and femur. A nonpathological angle of anteversion (AV angle) for the femoral neck is typically between 10 and 20 degrees. A malrotation with respect to the optimum (e.g., the other, healthy leg) of up to 10 degrees may be compensated by the patient, but larger malrotations may cause discomfort and problems when walking. Determining the AV angle intraoperatively is challenging and often performed incorrectly or not at all. Studies indicate that between 10% and 25% of osteosynthesis procedures on a leg produce deviations of more than 10 degrees from the ideal value. A reliable intraoperative procedure for determining the AV angle is therefore of great importance.

A difficulty of determining an angle of anteversion or torsion is that the long bones are too long to fit in one X-ray image. Moreover, the geometries required for determining the angle of anteversion or torsion are located at the most proximal and most distal parts of the bone, e.g., for the femur, the neck axis and the condyles. Hence, the geometries, which are depicted in separate proximal and distal X-ray images, must be related to each other.

The prior art proposes different approaches to determine the angle of anteversion. In case of a femur and a cephalomedullary nail, one approach is to determine by hand whether the knee is pointing upwards to the ceiling of the operating room and to judge subjectively whether the screw (or head element), which should intersect the nail axis and the center of the femoral head, makes an angle of approximately 10 degrees with the floor of the operating room. A CAS approach is proposed by Blau et al. (US 2015/0265361 A1 and WO 2019/077388 A1) where two reference bodies with metallic markers, one in the distal region and one in the proximal region of the femur, and two proximal X-ray images and one distal X-ray image, all depicting the respective reference body, are used.

Another difficult step in an intramedullary nailing procedure is locking. The main difficulty with locking using long nails is the nail's bending and torsion as the nail to some extent follows the medullary canal. This prevents a simple static mechanical locking procedure, which is employed in the case of short nails. Free-hand locking is challenging and time-consuming and may require acquisition of many X-ray images. For this reason, some manufacturers offer a flexible mechanical solution (here called "long aiming device") that adjusts to the bending of the nail. While a long aiming device simplifies the procedure, its application is still not straightforward because X-ray images showing the long aiming device must be interpreted correctly and the C-arm position adjusted accordingly. Only after correct adjustment of the C-arm may the long aiming device be adjusted properly.

Blau et al. (EP 2801320 A1) proposes a concept where a reference body with metallic markers at a fixed and known position relative to the long aiming device is detected, and the imaging direction onto the reference body is determined. Based on that, the system may give instructions on how to adjust the C-arm imaging device. The disadvantage of such a system is that the X-ray image must contain the reference body. For the adjustment of a long aiming device in case of an antegrade femur nail with locking holes in lateral direction, Blau et al. (US 2013/0211386 A1) uses a reference body in order to determine the bending of the nail in ML direction and in AP direction, respectively.

Reference bodies (or trackers) are commonly used in CAS systems. However, the use of reference bodies has several disadvantages, including added cost, more tedious handling, risk of user error, and a change of the usual surgery workflow. In addition, other objects, desirable features and characteristics will become apparent from the subsequent summary and detailed description, and the appended claims, taken in conjunction with the accompanying drawings and this background.

SUMMARY OF THE INVENTION

This invention proposes systems and methods, which require only a computer and display and/or loudspeaker, to process intraoperative 2D X-ray images to provide 3D geometric information about objects at least partially depicted in those X-ray images. It may be an object of the invention to provide a 3D representation of at least one object with respect to a coordinate system (e.g., relative to the image plane or relative to another object). It may also be an object of the invention to determine specific points or curves of interest on or within an object, possibly relative to another object. It may also be an object of the invention to provide a relative 3D orientation and 3D position between multiple objects at least partially depicted in the X-ray images.

As used herein, an "object" may be any object at least partially visible in an X-ray image, e.g., an anatomical structure, an implant, or a surgical tool. The present invention does not require the use of any reference body or tracker.

The term "3D representation" may refer to a complete or partial description of a 3D volume or 3D surface, and it may also refer to selected geometric aspects, such as a radius, a curve, a plane, an angle, or the like. The present invention may allow the determination of complete 3D information about the 3D surface or volume of an object, but methods that determine only selected geometric aspects are also considered in this invention.

Because X-ray imaging is a 2D imaging modality, it is not generally possible to uniquely determine the 3D pose (i.e., 3D position and 3D orientation) of individual objects depicted in an X-ray image, nor is it generally possible to uniquely determine the relative 3D position and 3D orientation between objects depicted in an X-ray image.

The physical dimensions of an object are related to the dimensions of its projection in an X-ray image through the intercept theorem because the X-ray beams originate from the X-ray source (the focal point) and are detected by an X-ray detector in the image plane. There is generally an ambiguity in determining the imaging depth, which is the distance from the image plane, also called "z-coordinate" in the sequel. Throughout this invention, the terms "localize" and "localization" mean a determination of the 3D orientation of an object with respect to the chosen coordinate system and a determination of the 2D spatial position of the projection of that object onto the image plane, but without determination of the z-coordinate.

If a 3D model of an object depicted in an X-ray image is available, this may allow localizing the object. Provided that the object is sufficiently big and has sufficient structure, it may even allow approximately determining (or estimating) the z-coordinate of that object. However, there are also cases where neither localization nor determination of the z-coordinate is possible, even though a deterministic 3D model of a known object shown in an X-ray image is available. As an example, this applies in particular to thin objects such as a drill or a k-wire. Without knowing the imaging depth of the drill's tip, there are multiple 3D poses of the drill that lead to the same or nearly the same projection in the 2D X-ray image. Hence, it may not generally be possible to determine the relative 3D position and 3D orientation of the drill relative to, say, an implant also shown in the X-ray image. On the other hand, if the imaging depth of such an object can be determined through other means or is known a priori, this may allow determining the 3D position and 3D orientation of that object.

It is an aim of the present invention to enable the localization of an object whose geometry is such that it may not be localizable without further information about its imaging depth, and to determine the 3D position and/or 3D orientation of such an object relative to another object.

One possible solution proposed by EP 19217245 is to utilize a priori information about the imaging depth. For example, it may be known, from a prior X-ray image acquired from a different imaging direction (which describes the direction in which the X-ray beam passes through the object), that the tip of the k-wire lies on the trochanter, thus restricting the imaging depth of the k-wire's tip relative to another object. This may be sufficient to resolve any ambiguity about the 3D position and 3D orientation of the k-wire relative to another object in the current imaging direction.

3D Registration of Two or More X-Rays

Another possible solution is to utilize two or more X-ray images acquired from different imaging directions and to register these images. The more different the imaging directions are (e.g., AP and ML images), the more helpful additional images may be in terms of a determination of 3D information. Image registration may proceed based on a uniquely localizable object depicted in the images whose 3D model is known, and which must not move between images. As mentioned above, the most common approach in the art is to use a reference body or tracker. However, it is generally preferable to not use any reference bodies because this simplifies both product development and use of the system. If the C-arm movements are precisely known (e.g., if the C-arm is electronically controlled), image registration may be possible solely based on these known C-arm movements.

However, C-arm movements are typically not known precisely. As described in LU101009B1, a rigid object of known geometry such as an implant may at least allow determining the imaging direction, even though an implant may only be localizable and may not allow determining the imaging depth.

Yet there are also many scenarios where no such rigid object is present in the X-ray image. For instance, when determining an entry point for implanting a nail, there is no implant in the X-ray image. The present invention teaches systems and methods that allow the 3D registration of multiple X-ray images in the absence of a single rigid object of known geometry that would generally allow unique and sufficiently accurate 3D registration. The approach proposed here is to use a combination of features of two or more objects or at least two or more parts of one object, each of which might not allow unique and sufficiently accurate 3D registration by itself, but which together enable such registration, and/or to restrict the allowable C-arm movements between the acquisition of images (e.g., only a rotation around a specific axis of an X-ray imaging device such as a C-arm axis, or a translation along a specific axis may be allowed). The objects used for registration may be man-made and of known geometry (e.g., a drill or a k-wire) or they may be parts of anatomy. The objects or parts of objects may also be approximated using simple geometrical models (for instance, the femoral head may be approximated by a ball), or only a specific feature of them may be used (which may be a single point, for instance, the tip of a k-wire or drill). The features of the objects used for registration must not move between the acquisition of images: if such a feature is a single point, then it is only required that this point not move. For instance, if a k-wire tip is used, then the tip must not move between images, whereas the inclination of the k-wire may change between images.

According to an embodiment, X-ray images may be registered, with each of the X-ray images showing at least a part of an object. A first X-ray image may be generated with a first imaging direction and with a first position of an X-ray source relative to the object. A second image may be generated with a second imaging direction and with a second position of the X-ray source relative to the object. Such two X-ray images may be registered based on a model of the object together with at least one of the following conditions:

A point with a fixed 3D position relative to the object is definable and/or detectable in both X-ray images, i.e., identifiable and/or localizable in both X-ray images. It is noted that a single point may be sufficient. It is further noted that the point may have a known distance to a structure of the object like the surface thereof.

Two identifiable points with a fixed 3D position relative to the object are in both X-ray images.

A part of a further object with a fixed 3D position is visible in both X-ray images. In such a case, a model of the further object may be utilized when registering the X-ray images. It is contemplated that even a point may be considered as the part of the further object.

Between the acquisition of the first and second X-ray images, the only movement of the X-ray source relative to the object is a translation.

Between the generation of the first and second X-ray images, the only rotation of the X-ray source is a rotation around an axis perpendicular to the imaging direction. For example, the X-ray source may be rotated around a C-axis of a C-arm based X-ray imaging device.

It will be understood that a registration of X-ray images based on a model of the object may be more accurate together with more than one of the mentioned conditions.

According to an embodiment, a point with a fixed 3D position relative to the object may be a point of a further object, allowing movement of the further object as long as the point is fixed. It will be understood that a fixed 3D position relative to an object may be on a surface of that object, i.e., a contact point, but may also be a point with a defined distance (greater than zero) from the object. That may be a distance from the surface of the object (which would allow a position outside or inside the object) or a distance to a specific point of the object (e.g., the center of the ball if the object is a ball).

According to an embodiment, a further object with a fixed 3D position relative to the object may be in contact with the object or at a defined distance to the object. It is noted that an orientation of the further object relative to the object may either be fixed or variable, wherein the orientation of the further object may change due to a rotation and/or due to a translation of the further object relative to the object.

It will be understood that a registration of X-ray images may also be performed with three or more objects.

According to various embodiments, the following are examples allowing an image registration (without reference body):

1. Using an approximation of a femoral head or an artificial femoral head (as part of a hip implant) by a ball (Object 1) and the tip of a k-wire or drill (Object 2), while also restricting the allowable C-arm movement between images.

2. Using an approximation of a bone shaft or a vertebral body by a cylinder (Object 1) and the tip of a k-wire or drill (Object 2), wherein the allowable C-arm movement may or may not be restricted between images.

3. Using an approximation of a femoral head or an artificial femoral head (as part of a hip implant) by a ball (Object 1) and an approximation of a femoral shaft by a cylinder (Object 2), wherein the allowable C-arm movement between images need not be restricted.

4. Using a guide rod (a guide rod has a stop that prevents it from being inserted too far) or k-wire fixated within a bone, while also restricting the allowable C-arm movement between images. In this case, only one object is used, and the method is embodied by the restricted C-arm movements between images.

5. Using a guide rod or k-wire (Object 1) fixated within a bone and an approximation of a femoral head by a ball (Object 2).

It is noted that this method may also be used to either enhance registration accuracy or to validate other results. That is, when registering images using multiple objects or at least multiple parts of an object, one or more of which might even allow 3D registration by itself, and possibly also restricting the allowable C-arm movements, this overdetermination may enhance registration accuracy compared to not using the proposed method. Alternatively, images may be registered based on a subset of available objects or features. Such registration may be used to validate detection of the remaining objects or features (which were not used for registration), or it may allow detecting movement between images (e.g., whether the tip of an opening instrument has moved).

Yet another embodiment of this approach may be to register two or more X-ray images that depict different (but possibly overlapping) parts of an object (e.g., one X-ray image showing the proximal part of a femur and another X-ray image showing the distal part of the same femur) by jointly fitting a model to all available X-ray projection images, while restricting the C-arm movements that are allowed between X-ray images (e.g., only translations are allowed). The model fitted may be a full or partial 3D model (e.g., a statistical shape or appearance model), or it may also be a reduced model that only describes certain geometrical aspects of an object (e.g., the location of an axis, a plane or select points).

As will be described in detail below, a 3D reconstruction of an object may be determined based on registered X-ray images. It will be understood that a registration of X-ray images may be performed and/or enhanced based on a 3D reconstruction of the object (or at least one of multiple objects). A 3D reconstruction determined based on registered X-ray images may be used for a registration of further X-ray images. Alternatively, a 3D reconstruction of an object may be determined based on a single or first X-ray image together with a 3D model of the object and then used when registering a second X-ray image with the first X-ray image.

Generally, a registration and/or 3D reconstruction of X-ray images may be of advantage in the following situations:

A determination of an angle of anteversion at a femur is of interest.

A determination of an angle of torsion at a tibia or humerus is of interest.

A determination of a CCD angle between head and shaft of a femur is of interest.

A determination of an antecurvation of a long bone is of interest.

A determination of a length of a bone is of interest.

A determination of an entry point for an implant at a femur, tibia or humerus is of interest.

In the following, examples of object combinations are listed for illustration.

Object 1 is a humeral head and a point is the tip of an opening instrument or a drill.

Object 1 is a vertebra and a point is the tip of an opening instrument or a drill positioned on the surface of the vertebra.

Object 1 is a tibia and a point is the tip of an opening instrument.

Object 1 is a tibia and object 2 is a fibula, a femur or a talus or another bone of the foot.

Object 1 is a proximal part of a femur and object 2 is an opening instrument at the surface of the femur.

Object 1 is a distal part of a femur and object 2 is an opening instrument at the surface of the femur.

Object 1 is a distal part of a femur and object 2 is a proximal part of the femur, wherein at least one X-ray image is depicting the distal part of the femur and at least one X-ray image is depicting the proximal part of the femur and a further object is an opening instrument positioned on the proximal part of the femur.

Object 1 is an Ilium and object 2 is a sacrum a point is the tip of an opening instrument or a drill Object 1 is an intramedullary nail implanted in a bone and object 2 is the bone.

Object 1 is an intramedullary nail implanted in a bone and object 2 is the bone and a point is the tip of an opening instrument, a drill or a sub-implant like a locking screw.

Computing a 3D Representation/Reconstruction

Once two or more X-ray images have been registered, they may be used to compute a 3D representation or reconstruction of the anatomy at least partially depicted in the X-ray images. According to an embodiment, this may proceed along the lines suggested by P. Gamage et al., "3D reconstruction of patient specific bone models from 2D radiographs for image guided orthopedic surgery," DOI: 10.1109/DICTA.2009.42. In a first step, features (typically characteristic bone edges, which may include the outer bone contours and also some characteristic interior edges) of the bone structure of interest are determined in each X-ray image, possibly using a neural network trained for segmentation. In a second step, a 3D model of the bone structure of interest is deformed such that its 2D projections fit the features (e.g., characteristic bone edges) determined in the first step in all available X-ray images. While the paper by Gamage et al. uses a generic 3D model for the anatomy of interest, other 3D models, e.g., a statistical shape model, may also be used. It is noted that this procedure not only requires the relative viewing angle between images (provided by the registration of images), but also the imaging direction for one of the images. This direction may be known (e.g., because the surgeon was instructed to acquire an image from a specific viewing direction, say, anterior-posterior (AP) or medial-lateral (ML)), or it may be estimated based on various approaches (e.g., by using LU100907B1). While the accuracy of the 3D reconstruction may be increased if the relative viewing angles between images are more accurate, the accuracy of determining the imaging direction for one of the images may not be a critical factor.

The accuracy of the determined 3D representation may be enhanced by incorporating prior information about the 3D position of one or more points, or even a partial surface, on the bone structure of interest. For instance, in the 3D reconstruction of a femur with an implanted nail, a k-wire may be used to indicate a particular point on the femur's surface in an X-ray image. From previous procedural steps, the 3D position of this indicated point in the coordinate system given by the implanted nail may be known. This knowledge may then be used to more accurately reconstruct the femur's 3D surface. If such a priori information about the 3D position of a particular point is available, this may even allow a 3D reconstruction based on a single X-ray image. Moreover, in case an implant (such as a plate) matches the shape of part of a bone and has been positioned on this matching part of the bone, this information may also be used for 3D reconstruction.

As an alternative approach, 3D reconstruction of an object (e.g., a bone) may also be performed without prior image registration, i.e., image registration and 3D reconstruction may also be performed jointly as suggested by LU101009B1. It is taught in this disclosure to increase accuracy and resolve ambiguities by restricting allowable C-arm movements and/or utilizing an easily detectable feature of another object (e.g., a drill or k-wire) present in at least two of the images on which joint registration and reconstruction is based. Such an easily detectable feature may for instance be the tip of a k-wire or drill, which either lies on the surface of the object to be reconstructed or at a known distance from it. This feature must not move between the acquisition of images. In the case of a k-wire or drill, this means that the instrument itself may change its inclination, as long as its tip remains in place. Reconstruction without prior image registration may work better if more than two images are being used for such reconstruction. It is noted that a joint image registration and 3D reconstruction may in general outperform an approach where registration is performed first because a joint registration and 3D reconstruction allows joint optimization of all parameters (i.e., for both registration and reconstruction). This holds in particular in the overdetermined case, for instance, when reconstructing the 3D surface of a bone with implanted nail or plate and a priori information about the 3D position of a point on the surface.

For a joint image registration and 3D reconstruction, a first X-ray image showing a first part of a first object may be received, wherein the first X-ray image is generated with a first imaging direction and with a first position of an X-ray source relative to the first object, and at least a second image showing a second part of the first object may be received, wherein the second X-ray image is generated with a second imaging direction and with a second position of the X-ray source relative to the first object. By using a model of the first object, the projections of the first object in the two X-ray images may be jointly matched so that the spatial relation of the images can be determined because the model can be deformed and adapted to match the appearances in the X-ray images. The result of such joint registration and 3D reconstruction may be enhanced by at least one point having a fixed 3D position relative to the first object, wherein the point is identifiable and detectable in at least two of the X-ray images (it will be understood that more than two images may also be registered while improving the 3D reconstruction). Furthermore, at least a part of a second object with a fixed 3D position relative to the first object may be taken into account, wherein based on a model of the second object the at least partial second object may be identified and detected in the X-ray images.

It is noted that the first part and the second part of the first object may overlap, which would enhance the accuracy of the result. For example, the so-called first and second parts of the first object may be both a proximal portion of a femur, wherein the imaging direction differs so that at least the appearance of the femur differs in the images.

Determining an Implantation Curve and/or Entry Point

It may be an aim of this invention to determine an implantation curve or path, along which an implant such as a nail or a screw may be inserted and implanted into a bone, and/or to determine an entry point, which is the point at which the surgeon opens the bone for inserting the implant. The entry point is thus the intersection of the implantation curve with the bone surface. The implantation curve may be a straight line (or axis), or it may also be bent because an implant (e.g., a nail) has a curvature. It is noted that the optimal location of the entry point may depend on the implant and also the location of a fracture in the bone, i.e., how far in distal or proximal direction the fracture is located.

There are various instances in which an implantation curve and/or an entry point may have to be determined. In some instances, in particular, if a full anatomical reduction has not yet been performed, only an entry point might be determined. In other instances, an implantation curve is obtained first, and an entry point is then obtained by determining the intersection of the implantation curve with the bone surface. In yet other instances, an implantation curve and an entry point are jointly determined. Examples for all of these instances are discussed in this invention.

In general, a 2D X-ray image is received in accordance with an embodiment, which X-ray image shows a surgical region of interest. In that X-ray image, a first point associated with a structure of interest as well as an implantation path within the bone for an implant intended to be implanted may be determined, wherein the implantation curve or path has a predetermined relation to the first point. An entry point for an insertion of the implant into the bone is located on the implantation path. It will be understood that the first point may not be the entry point.

Freehand Locking Procedure

Based on the mentioned general determination of a point and an implantation path in an 2D X-ray image, the following condition may be fulfilled for the predetermined relation between the implantation path and the point, when considering an implantation of a screw for locking of e.g. a bone nail: When the structure of interest is a hole in an implant, the hole may have a predetermined axis and the point may be associated with a center of the hole and the implantation path may point in the direction of the axis of the hole.

As a possible application, an example workflow for a freehand locking procedure, where an implant is locked by implanting a screw through a hole of the implant, is described. According to an embodiment, the already implanted nail is localized in X-ray images, which determines the implantation curve. Here, the implantation curve is a straight line (axis), along which the screw is implanted. A 3D reconstruction of the bone surface (at least in the vicinity of the implantation curve) may be performed relative to the already implanted nail (i.e., in the coordinate system given by the nail). This may proceed as follows. At least two X-ray images are acquired from different viewing directions (e.g., one AP or ML image and one image taken from an oblique angle). The X-ray images may be classified by a neural net e.g. regarding and registered using, e.g., the implanted nail, and the bone contours are segmented in all images possibly by a neural net. A 3D reconstruction of the bone surface may be possible following the 3D reconstruction procedure outlined above. The intersection of the implantation curve with the bone surface determines the 3D position of the entry point relative to the nail. Since the viewing direction in an X-ray image may be determined based on the localized nail, this also allows indicating the location of the entry point in the given X-ray images.

It may be possible to increase the accuracy of this procedure by incorporating a known 3D position of at least one point on the bone surface relative to the nail. Such knowledge may be obtained by combining the procedure in the present invention with the freehand locking procedure taught by EP 19217245. A possible approach may be to use EP 19217245 to obtain the entry point for a first locking hole, which then becomes a known point on the bone surface. This known point may be used in the present invention for the 3D reconstruction of the bone and subsequent determination of the entry point for a second and further locking holes. A point on the bone surface may also be identified, e.g., by a drill tip touching the bone surface. If a point is identified in more than one X-ray image taken from different imaging directions, this may increase accuracy.

Determining an Entry Point for Implanting a Nail into a Femur

Based on the mentioned general determination of a first point and an implantation path in a 2D X-ray image, at least one of the following conditions may be fulfilled for the predetermined relation between the implantation path and the first point when considering an implantation of a nail into a femur:

When the structure of interest is a femur head, the first point may be associated with a center of the femur head and may consequently be located on a proximal extension of the implantation path, i.e., proximally relative to the entry point in the X-ray image.

When the structure of interest is a narrow portion of a femur neck, the first point may be associated with a center of a cross-section of the narrow portion of the femur neck, and a proximal extension of the implantation path may in said narrow portion be closer to the first point than to an outer surface of the femur neck.

When the structure of interest is a narrow portion of a femur shaft, the first point may be associated with a center of a cross-section of the narrow portion at the proximal end of a femur shaft, and the implantation path may in said narrow portion be closer to the first point than to an outer surface of the femur shaft.

When the structure of interest is an isthmus of a femur shaft, the first point may be associated with a center of a cross-section of the isthmus, and the first point may be located on the implantation path.

In embodiments, it is not necessary that a structure of interest be fully visible in the X-ray image. It may be sufficient to have only 20 percent to 80 percent of the structure of interest visible in the X-ray image. Depending on the specific structure of interest, i.e., whether the structure of interest is a femur head, a femur neck, a femur shaft or another anatomical structure, at least 30 to 40 percent of the structure must be visible. In consequence, it may be possible to identify e.g., a center of a femur head even if that center itself is not visible in the X-ray image, i.e., lies outside the imaged area, even in a case in which only 20 percent to 30 percent of the femur head is visible. The same is possible for the isthmus of the femur shaft, even if the isthmus lies outside the imaged area and only 30 to 50 percent of the femur shaft is visible.

To detect points of interest in an image, a neural segmentation network, which classifies each pixel whether it is a potential keypoint, may be used. A neural segmentation network can be trained with a 2D Gaussian heatmap with the center located at the true keypoint. The Gaussian heatmap may be rotationally invariant or, if an uncertainty in a particular direction is tolerable, the Gaussian heatmap may also be directional. To detect points of interest outside the image itself, one possible approach may be to segment additional pixels outside the original image, using all information contained in the image itself to allow extrapolation.

An example workflow for determining an entry point for implanting an intramedullary or cephalomedullary nail into a femur is presented. According to an embodiment, first the projection of an implantation curve is determined for an X-ray image. In this embodiment, the implantation curve is approximated by a straight line (i.e., an implantation axis). As a first step, it may be checked whether the present X-ray image satisfies necessary requirements for determining the implantation axis. These requirements may include image quality, sufficient visibility of certain areas of anatomy, and an at least approximately appropriate viewing angle (ML) onto anatomy. Further, the requirements may include whether the above-mentioned conditions are fulfilled. These requirements may be checked by an image processing algorithm, possibly utilizing a neural network. Furthermore, if applicable, the relative positions of bone fragments may be determined and compared with their desired positions, based on which it may be determined whether these fragments are sufficiently well arranged (i.e., an anatomical reduction has been performed sufficiently well).

In more detail, the above-mentioned conditions may be described as follows. An implantation axis is determined by one point and a direction, which are associated with at least two anatomical landmarks (e.g., these may be the center of the femoral head and the isthmus of the femoral shaft). As described above, a landmark may be determined by a neural network even if it is not visible in the X-ray image. Whether or not a suggested implantation axis is acceptable may be checked by determining the distances from the suggested axis to various landmarks on the bone contour as visible in the X-ray. For instance, the suggested implantation axis should pass close to the center of the femoral neck isthmus, i.e., it should not be too close to the bone surface. If such a condition is violated, the X-ray image was not acquired from a suitable imaging direction, and another X-ray image from a different imaging direction must be acquired. Determining the implantation curve in another X-ray image from a different viewing direction may result in a different implantation axis and thus may result in a different entry point. The present invention also teaches how to adjust the imaging device in order to acquire an X-ray image from a suitable direction.

It is noted that an implant may have a curvature, which means that a straight implantation axis may only approximate the projection of the inserted implant. The present invention may also instead determine an implantation curve that more closely follows the 2D projection of an implant, based on a 3D model of the implant. Such an approach may use a plurality of points associated with two or more anatomical landmarks to determine an implantation curve.

The projection of an implantation axis determines an implantation plane in 3D space (or more generally, the projection of an implantation curve determines a two-dimensional manifold in 3D space). The entry point may be obtained by intersecting this implantation plane with another bone structure that may be approximated by a line and is known to contain the entry point. In the case of a femur, such a bone structure may be the trochanter rim, which is narrow and straight enough to be well approximated by a line, and on which the entry point may be assumed to lie. It is noted that, depending on the implant, other locations for the entry point may be possible, for instance, on the *piriformis* fossa.

The trochanter rim may be detectable in a lateral X-ray image. Alternatively, or additionally, another point identifiable in the image (e.g., the tip of a depicted k-wire or some other opening tool) may be utilized, for which some prior information about its position relative to the entry point is known. In the case of a femur, an example for this would be if it is known that the tip of a k-wire lies on the trochanter rim, which may be known by palpating and/or because a previously acquired X-ray from a different viewing angle (e.g., AP) restricts the location of the k-wire's tip in at least one dimension or degree of freedom.

There may be at least three ways of utilizing such prior information about a k-wire's (or some other opening instrument's) tip relative to the entry point. The easiest possibility may be to use the orthogonal projection of the k-wire's tip onto the projection of the implantation axis. In this case it may be required to check in a subsequent X-ray image acquired from a different angle (e.g., AP) whether the k-wire tip still lies on the desired structure (the trochanter rim) after repositioning the k-wire tip based on the information in the ML image and possibly acquiring a new ML image after repositioning. Another possibility may be to estimate the angle between the projection of the structure (which may not be identifiable in an ML image) and the projection of the implantation axis based on anatomical a priori information, and to obliquely project the k-wire's tip onto the projection of the implantation axis at this estimated angle. Finally, a third possibility may be to use a registered pair of AP and ML images to compute in the ML image the intersection of the projected epipolar line defined by connecting the k-wire tip and the focal point of the AP image with the projected implantation axis. Once an entry point has been obtained, this also determines the implantation axis in 3D space.

Alternatively, the bone structure (here, the trochanter rim), whose intersection with the implantation plane determines the entry point, may also be found by performing a partial 3D reconstruction of the proximal femur. According to an embodiment, this 3D reconstruction may proceed as follows, based on two or more X-ray images from different viewing directions, at least two of which contain a k-wire. Characteristic bone edges (comprising at least bone contours) of the femur are detected in all X-ray images. Furthermore, in all X-ray images, the femoral head is found and approximated by a circle, and the k-wire's tip is detected. The images may now be registered using the approach presented above, based on the characteristic bone edges, the approximated femoral head and the k-wire's tip, and a restricted C-arm movement. After image registration, the 3D surface containing at least the trochanter area may be reconstructed. Accuracy of the 3D reconstruction may be increased by utilizing prior information about the distance of the k-wire's tip from the bone surface (which may be known, e.g., from an AP image). Various alternatives to this procedure may be possible, which are described in the detailed description of the embodiments.

In the preceding approach, the implantation curve is determined in a 2D X-ray image, and then various alternatives for obtaining the entry point are discussed. Alternatively, the entire procedure (i.e., determination of implantation curve and entry point) may be based on a 3D reconstruction of the proximal femur (or distal femur if using a retrograde nail), including a sufficient portion of the shaft. Such a 3D reconstruction may again be based on a plurality of X-ray images, which have been registered using the method presented above. For instance, registration may use the approximation of the femoral head by a ball, and the approximation of the shaft by a cylinder or a mean shaft shape. Alternatively, a joint optimization and determination of registration and bone reconstruction (which may comprise the surface and possibly also inner structures like the medullary canal and the inner cortices) may be performed. Once a 3D reconstruction of the relevant part of the femur has been obtained, a 3D implantation curve may be fitted by optimizing the distances between the implant surface and the bone surface. The intersection of the 3D implantation curve with the already determined 3D bone surface yields the entry point.

A position and orientation of an implantation curve in relation to the 2D X-ray image is determined on the basis of a first point, wherein the implantation curve comprises a first section within the bone with a first distance to a surface of the bone and a second section within the bone with a second distance to the surface of the bone, wherein the first distance is smaller than the second distance, and wherein the first point is located on a first identifiable structure of the bone and is located at a distance to the first section of the implantation axis. A second point may be utilized which may be located on an identifiable structure of the bone and may be located at a distance to the second section of the implantation curve. Furthermore, the position and orientation of the implantation curve may further be determined on the basis of at least one further point, wherein the at least one further point is located on a second identifiable structure of the bone and is located on the implantation curve.

Determining an Entry Point for Implanting a Nail into a Tibia

Based on a joint registration and 3D reconstruction as described in the section "Computing a 3D representation/reconstruction" above, an entry point for implanting an intramedullary nail into a tibia may be determined.

According to an embodiment, it is suggested to increase accuracy and resolve any ambiguities by requiring that the user place an opening instrument (e.g., a drill or a k-wire) onto the surface of the tibia at an arbitrary point of the proximal part, but ideally in the vicinity of the suspected entry point. The user acquires a lateral image and at least one AP image of the proximal part of the tibia. A 3D reconstruction of the tibia may be computed by jointly fitting a statistical model of the tibia to its projections of all X-ray images, taking into account the fact that the opening instrument's tip does not move between images. Accuracy may be further increased by requiring that the user acquire two or more images from different (e.g. approximately AP) imaging directions, and possibly also another (e.g., lateral) image. Any overdetermination may allow detecting a possible movement of the tip of the opening instrument and/or validate the detection of the tip of the opening instrument.

Based on the 3D reconstruction of the tibia, the system may determine an entry point, for instance, by identifying the entry point on the mean shape of the fitted statistical model. It is noted that such guidance for finding the entry point for an antegrade tibia nail solely based on imaging (i.e., without palpation) may enable a surgeon to perform a suprapatellar approach, which may generally be preferrable but conventionally has the disadvantage that a palpation of the bone at the entry point is not possible.

Determining an Entry Point for Implanting a Nail into a Humerus

A further application of the proposed image registration and reconstruction techniques presented above may be the determination of an entry point for implanting an intramedullary nail into a humerus.

In general, a system comprising a processing unit for processing X-ray images may be utilized for assisting in humerus surgery based on X-ray images so as to achieve the mentioned aim. A software program product, when executed on the processing unit, may cause the system to perform a method including the following steps. Firstly, a first X-ray image is received having been generated with a first imaging direction and showing a proximal portion of a humerus, and a second X-ray image is received having been generated with a second imaging direction and showing the proximal portion of the humerus. Those images may include the proximal portion of the humerus shaft as well as the humerus head with the joint surface and further the glenoid, i.e., the complementary joint structure at the shoulder. It is noted that the second imaging direction typically differs from the first imaging direction. Then, (i) the first and second X-ray images are registered, (ii) an approximation of at least a part of the 2D outline of the humerus head in both images is determined, (iii) a 3D approximation of the humerus head based on the approximated 2D outlines and the registration of the first and second images is determined, (iv) 2D image coordinates of a total of at least three different points in the first and second X-ray images are determined. Finally, an approximation of an anatomical neck is determined as a curve on the 3D approximation of the humerus head based on the at least three determined points. It is noted that the at least three determined points need not lie on the determined curve. An even more accurate approximation of the ana- tomical neck may be determined if it is possible to determine additional points of the anatomical neck which are not located in the same plane as the first three points. This may allow determining the rotational position of the anatomical neck and thus the humerus head around the shoulder joint axis. Another way to determine the rotational position around the joint axis may be to detect the position of a tuberculum major and/or tuberculum minor in case that at least one of the two is in fixed position relative to the proximal fragment. Another alternative may be to use pre- operatively acquired 3D information (e.g., a CT scan) to generate a 3D reconstruction of the proximal fragment based on intraoperative X-ray images. This method may be com- bined with the methods mentioned above.

According to an embodiment, the approximation of at least a part of the 2D outline of the humerus head may be a 2D circle or 2D ellipse. Furthermore, the 3D approximation of the humerus head may be a 3D ball or 3D ellipsoid. The approximation of the anatomical neck may be a circle or an ellipse in 3D space.

According to an embodiment, a further X-ray image may be received and an approximation of a humerus shaft axis in at least two of the X-ray images out of the group consisting of the first X-ray image, the second X-ray image, and the further X-ray image may be determined. Based on the approximated humerus shaft axes in the at least two X-ray images together with the registration of the first and second X-ray images, an approximation of a 3D shaft axis of the humerus may be determined.

According to an embodiment of the disclosed method, an entry point and/or a dislocation of a proximal fragment of a fractured humerus may then be determined based on the approximated anatomical neck and the approximated 3D shaft axis and/or an approximated glenoid of a humerus joint. In consequence, an implantation curve may be deter- mined in a proximal fragment based on the entry point and the dislocation of the head. Furthermore, information may be provided for repositioning the proximal fragment.

According to an embodiment, at least two X-ray images may be registered, wherein these two X-ray images may be two out of the first X-ray image, the second X-ray image, and the further X-ray image. The X-ray images may be registered based on a model of the humerus head and based on one additional point having a fixed 3D position relative to the humerus head, wherein the point is identified and detected in the at least two X-ray images. The one additional point may be the tip of an instrument and may be located on a joint surface of the humerus head. In this case the fact that the distance between the point and the humeral head center equals the radius of the humeral head approximated by a ball may be utilized to enhance the accuracy of the registration of the x-ray images.

In the following, aspects of a method according to the disclosure are described in more detail. The humeral head sitting in the shoulder joint may be approximated by a ball (sphere). In the following, unless stated otherwise, it is understood that the humerus is approximated by such a ball, which means approximating the projection of a humerus in an X-ray image by a circle. Hence, "center" and "radius" always refer to such an approximating ball or circle. It is noted that it may also be possible to use other simple geometrical approximations of the humerus head, e.g., by an ellipsoid. In that case, the anatomical neck would be approximated by an ellipse.

The following describes an example workflow for entry point determination. A complicating problem in determining an entry point in the humerus is that fractures treated with a humeral nail frequently occur along the surgical neck, thus displacing the humeral head. In a correct reduction, the center of the humeral head should be close to the humerus shaft axis. According to an embodiment, this may be verified in an axial X-ray image depicting the proximal humerus. If the center of the humeral head is not close enough to the shaft axis, the user is advised to apply traction force to the arm in distal direction in order to correct any rotation of the humeral head around the joint axis (which may not be detectable). An approximate entry point is then suggested on the shaft axis approximately 20% medial to (meaning in a typical axial X-ray image above) the center of the head. The user is then required to place an opening instrument (e.g., a k-wire) on this suggested entry point. Alternatively, in order to enhance the accuracy of the registration as described above, the system asks the user to place the opening instru- ment intentionally medial to the suspected entry point (meaning 30 to 80 percent above the depicted center of the femoral head in the axial X-ray image) in order to make sure that the tip of the instrument is located on the spherical part of the humerus head. The system may detect the humeral head and the tip of this instrument (e.g., by using neural networks) in a new axial X-ray image.

The user is then instructed to acquire an AP image, allowing only certain C-arm movements (e.g., rotation around the C-axis and additional translations) and leaving the tip of the instrument in place (the inclination of the instrument is allowed to change). The humeral head and the tip of the instrument are again detected. The axial and the AP image may then be registered as described above in the section "3D registration of two or more X-rays" based on the ball approximating the humeral head and the tip of the instrument.

The curve delimiting the shoulder joint's articular surface is called the anatomical neck (collum anatomicum). The anatomical neck delimits the spherical part of the humerus, but it is typically impossible to identify in the X-ray by a surgeon. It may be approximated by a 2D circle in 3D space, which is obtained by intersecting a plane with the ball approximating the humeral head, wherein the plane is inclined relative to the shaft axis of the humerus. The spherical joint surface is oriented upwardly (valgus) and dorsally (with the patient's arm hanging relaxed down- wardly from the shoulder and parallel to the chest). Three points are sufficient to define this intersecting plane. The axial X-ray and the AP X-ray may each allow determining two points on the anatomical neck, namely the start and end points of the arc of the circle that delimit the spherical part of the humerus. This is therefore an overdetermined problem: based on two X-ray images, four points may be determined whereas only three points are necessary to define the intersecting plane. If additional X-ray images are used, the problem may become more overdetermined. This overdetermination may either allow a more precise calculation of the intersecting plane, or it may allow handling a situation where a point may not be determined, for instance, because it is occluded.

It is noted that, when determining an approximation of the anatomical neck by intersecting the determined plane with the ball approximating the humeral head, various modifications may be possible. For instance, the intersecting plane may be shifted in lateral direction to account for a more precise location of the anatomical neck on the humerus head. Alternatively, or additionally, the radius of the circle approximating the anatomical neck may be adjusted. It may also be possible to use geometrical models with more degrees of freedom to approximate the humerus head and/or to approximate the anatomical neck.

The entry point may be taken to be the point on the anatomical neck that is closest in 3D space to the intersection of the shaft axis and bone surface, or it may be located at a user-defined distance from that point in medial direction. The thus determined anatomical neck and entry point may be displayed as an overlay in the current X-ray image. If this entry point is very close to the circle approximating the head in the X-ray image, this would result in a potentially large inaccuracy in the z-coordinate. In order to alleviate such a situation, instructions may be given to rotate the C-arm such that the suggested entry point moves further toward the interior of the head in the X-ray image. This may be advantageous in any case because it may be difficult, due to mechanical constraints, to acquire an X-ray image where the entry point is located close to the approximating circle. In other words, the rotation of the C-arm between axial and AP images may, e.g., be by 60 degrees, which may be easier to achieve in the surgical workflow than a 90-degree rotation.

Further details, optional implementations, and extensions of this workflow are described in the detailed description of the embodiments below.

Reduction Support

Another aim of this invention may be to support an anatomically correct reduction of bone fragments. Typically, a surgeon will try to reposition fragments of a bone fracture in a relative arrangement that is as natural as possible. For an improved result, it may be of interest to check whether such a reduction was anatomically correct before or after inserting any implant for fixation.

Reduction may be supported by computing a 3D reconstruction of a bone of interest. Such a 3D reconstruction may not have to be a complete reconstruction of the entire bone and may not have to be precise in every aspect. In case only a specific measurement is to be extracted, the 3D reconstruction only needs to be precise enough to allow a sufficiently accurate determination of this measurement. For instance, if the femoral angle of anteversion (AV) is to be determined, it may suffice to have a 3D reconstruction of the femur that is sufficiently accurate in the condyle and neck regions. Other examples of measures of interest may include a length of a leg, a degree of a leg deformity, a curvature (like the antecurvation of a femur) or a caput-collum-diaphysis (CCD) angle as there is often a varus rotation of the proximal fragment of the femur that occurs before or after the insertion of an intramedullary nail. Once a measure of interest has been determined, it may be used to select an appropriate implant, or it may be compared with a desired value, which may be derived from a database or be patient-specific, e.g., by comparing the leg being operated on with the other healthy leg. Instructions may be given to the surgeon on how to achieve a desired value, e.g., a desired angle of anteversion.

It may also be of interest to monitor a certain measure throughout the surgery by automatically computing it from available X-ray images and to possibly warn the surgeon in case the measure deviates too much from a desired value.

In some cases, a 3D reconstruction may be possible even from a single X-ray image, in particular, if the viewing direction can be determined (e.g., based on LU100907B1) and only a specific measurement (e.g., a CCD angle) is of interest. In general, however, two or more X-ray images, taken from different viewing directions and/or depicting different parts of the bone, may increase accuracy of a 3D reconstruction (cf. the section "Computing a 3D representation/reconstruction" above). A 3D reconstruction may be computed even of parts of the bone that are not or only partially visible in the X-ray images, provided that the non-visible part is not displaced with respect to the visible part due to a fracture or, in case that there is such a displacement, the dislocation parameters are already known or can be otherwise determined. For instance, based on a statistical 3D model of the femur, the femoral head may be sufficiently accurately reconstructed from a pair of ML and AP images where the majority of the femoral head is not visible. As another example, the distal part of the femur may be reconstructed based on two proximal X-rays if the femur shaft is not fractured. Of course, accuracy of the reconstruction of the distal part can be increased if a further X-ray, showing the distal part, is also available.

In the 3D reconstruction of a bone based on two or more X-ray images, accuracy may be further increased if these X-ray images can be registered before computing the 3D reconstruction, following one of the approaches described in the section "3D registration of two or more X-rays" above. In a case where a 3D reconstruction of a bone is to be computed based on two or more X-rays that show different parts of the bone (e.g., two X-rays showing the proximal part of a femur and one X-ray showing the distal part of this femur), a 3D registration of the X-rays depicting different parts may be possible based on an object with known 3D model (e.g., an already implanted nail) that is visible in at least one X-ray for each bone part and/or by restricting the allowable C-arm movements between the acquisition of those X-rays (see LU101009B1).

The AV angle may have to be determined when an implant has not yet been inserted, either before or after opening the patient (e.g., in order to detect a dorsal gap in a reduction of a pertrochanteric fracture). In such a case, registration of two or more images of the proximal femur (e.g., AP and ML) may proceed along the lines of the section "3D registration of two or more X-rays" above, as follows. When determining an entry point for inserting a nail, an opening instrument such as a k-wire (whose diameter is known) may be placed on a suspected entry point and thus be detected in the X-ray images. Based on the position of its tip and together with a detected femoral head, the images may be registered. In case no further object like a k-wire is visible in the X-ray image, a registration of images may still be performed by requiring a specific movement of the C-arm between the images. For instance, the system may require a rotation around the C-axis of the C-arm by 75 degrees. If this rotation is performed with sufficient accuracy, a registration of the images is also possible with sufficient accuracy. Non-overlapping parts of the bone (for instance, the distal and the proximal parts of a femur) may be registered by restricting the allowed C-arm movements to translational movements only, as described in an embodiment.

It is noted that a 3D reconstruction is not necessary to determine an AV angle. By determining one further point, e.g., in the vicinity of the neck axis, there may be enough information to determine the AV angle based on a 2D approach. A registration of 2D structures detected in X-ray images (e.g., structures within a proximal and a distal part of a femur) may be done by employing the above method.

In other instances, it may be beneficial to take into account neighboring bones or bone structures e.g., when determining the correct rotation angle of a bone. For example, in case of a fractured tibia, the evaluation of the orientation of its proximal part may consider the condyles of the femur, the patella, and/or the fibula. Similar comments apply to evaluating the rotational position of its distal part. The relative position of the tibia to the fibula or other bone structures (e.g., overlapping edges of joints in the foot) may clearly indicate the viewing direction onto the distal tibia. All these evaluations may be based on a neural network, which may perform a joint optimization, possibly based on confidence values (of correct detection) for each considered structure. The results of such evaluations may be combined with knowledge about patient or extremity positioning to evaluate the current reduction of a bone. For example, in case of a humerus, the system may instruct the surgeon to position a patient's radius bone parallel to the patient's body. For reduction evaluation, it may then suffice to guide the user to achieve a centered position of the humeral joint surface relative to the glenoid by detecting these structures in the X-ray image.

Reduction of X-Ray Dosage

It may be kept in mind that an overall object may be a reduction of X-ray exposure to patient and operating room staff. As few X-ray images as possible should be generated during a fracture treatment in accordance with the embodiments disclosed herein. For instance, an image acquired to check a positioning of a proximal fragment relative to a distal fragment may also be used for a determination of an entry point. As another example, images generated in the process of determining an entry point may also be used to measure an AV angle or a CCD angle.

X-ray exposure may also be reduced because, according to an embodiment, it is not necessary to have complete anatomical structures visible in the X-ray image. A 3D representation or localization of objects such as anatomical structures, implants, surgical tools, and/or parts of implant systems may be provided even if they are not or only partially visible in the X-ray image. As an example, even if the projection image does not fully depict the femoral head, it may still be completely reconstructed. As another example, it may be possible to reconstruct the distal part of a femur based on one or more proximal images, with the distal part not fully depicted.

In some cases, it may be necessary to determine a point of interest associated with an anatomical structure, e.g., the center of a femoral head or a particular point on a femur shaft. In such a case, it may not be necessary that the point of interest is shown in the X-ray image. This applies a fortiori in cases where any uncertainty or inaccuracy in determining such a point of interest affects a dimension or degree of freedom that is of less importance in the sequel. For example, the center point of the femoral head and/or a particular point on the axis of the femur shaft may be located outside of the X-ray image, but based on, e.g., a deep neural network approach, the system may still be able to determine those points and utilize them, e.g., to compute an implantation curve with sufficient accuracy because any inaccuracy in the direction of the implantation curve may not have a significant impact on the computed implantation curve.

According to an embodiment, the processing unit of the system may be configured to determine an anatomical structure and/or a point of interest associated with the anatomical structure on the basis of an X-ray projection image showing a certain minimally required percentage (e.g., 20%) of the anatomical structure. If less than the minimally required part of the anatomical structure is visible (e.g., less than 20%), the system may guide the user to obtain a desired view. As an example, if the femoral head is not visible at all, the system may give an instruction to move the C-arm in a direction computed based on the appearance of the femoral shaft in the current X-ray projection image.

Matching a 3D Model to a 2D Projection Image

It is noted that the image data of the processed X-ray image may be received directly from an imaging device, for example from a C-arm or G-arm based 2D X-ray device, or alternatively from a database. The X-ray projection image may represent an anatomical structure of interest, in particular, a bone. The bone may for example be a bone of a hand or foot, but may in particular be a long bone of the lower extremities, like the femur and the tibia, and of the upper extremities, like the humerus. The image may also include an artificial object like a bone implant or a surgical tool, e.g., a drill or a k-wire.

This disclosure differentiates between an "object" and a "model". The term "object" will be used for a real object, e.g., for a bone or part of a bone or another anatomical structure, or for an implant like an intramedullary nail, a bone plate or a bone screw, or for a surgical tool like a sleeve or k-wire. An "object" may also describe only part of a real object (e.g., a part of a bone), or it may be an assembly of real objects and thus consist of sub-objects (e.g., an object "bone" may be fractured and thus consist of sub-objects "fractured bone parts").

On the other hand, the term "model" will be used for a virtual representation of an object. For example, a dataset defining the shape and dimensions of an implant may constitute a model of an implant. As another example, a 3D representation of an anatomical structure as generated for example during a diagnostic procedure may be taken as a model of a real anatomical object. It should be noted that a "model" may describe a particular object, e.g., a particular nail, or it may describe a class of objects, such as a femur, which have some variability. In the latter case, such objects may for instance be described by a statistical shape or appearance model. It may then be an aim of the invention to find a 3D representation of the particular instance from the class of objects that is depicted in the acquired X-ray image. For instance, it may be an aim to find a 3D representation of the femur depicted in an acquired X-ray image based on a general statistical shape model of femurs. It may also be possible to use a model that contains a discrete set of deterministic possibilities, and the system would then select which one of these best describes an object in the image. For instance, there could be several nails in a database, and an algorithm would then identify which nail is depicted in the image.

It is noted that a model may be a complete or a partial 3D model of a real object, or it may only describe certain geometrical aspects of an object (which may also be of dimension smaller than 3), such as the fact that the femoral or humeral head can be approximated by a ball in 3D and a circle in the 2D projection image, or the fact that a shaft has a direction described by a shaft axis.

Since a 3D representation is actually a set of computer data, it is easily possible to extract specific information like geometrical aspects and/or dimensions of the virtually represented object from that data (e.g., an axis, an outline, a curvature, a center point, an angle, a distance, or a radius). If a scale has been determined based on one object, e.g., because a width of a nail is known from model data, this may also allow measuring a geometrical aspect or dimension of another depicted and potentially unknown object if such object is located at a similar imaging depth. It may even be possible to calculate a size of a different object at a different imaging depth based on the intercept theorem if the imaging depth of one object is known (e.g., because that object is sufficiently big or because the size of the X-ray detector and the distance between image plane and focal point is known) and if there is information about the differences in imaging depths between the two objects (e.g., based on anatomical knowledge).

According to an embodiment, objects in the X-ray image are automatically classified and identified in an X-ray projection image. However, an object may also be manually classified and/or identified in the X-ray projection image. Such a classification or identification may be supported by the device by automatically referring to structures that were recognized by the device.

Matching the model of an object to its projection depicted in an X-ray image may consider only selected features of the projection (e.g., contours or characteristic edges) or it may consider the entire appearance. Contours or characteristic edges may be determined using a neural segmentation network. The appearance of an object in an X-ray image depends inter alia on attenuation, absorption, and deflection of X-ray radiation, which in turn depend on the object's material. For instance, a nail made of steel generally absorbs more X-ray radiation than a nail made of titanium, which may affect not only the appearance of the nail's projection image within its outline, but it may also change the shape of the outline itself, e.g., the outline of the nail's holes. The strength of this effect also depends on the X-ray intensity and the amount of tissue surrounding the object, which the X-ray beam must pass through. As another example, a transition between soft and hard tissue may be identifiable in an X-ray image, since such transition cause edges between darker and lighter areas in the X-ray image. For example, a transition between muscle tissue and bone tissue may be an identifiable structure, but also the inner cortex, a transition between spongious inner bone tissue and the hard cortical outer bone tissue, may be identifiable as a feature in the X-ray image. It is noted that wherever in this disclosure an outline of a bone is determined, such an outline may also be the inner cortex or any other identifiable feature of the bone shape.

According to an embodiment, for objects described by a deterministic model, a 2D-3D matching may proceed along the lines described by Lavallée S., Szeliski R., Brunie L. (1993) Matching 3-D smooth surfaces with their 2-D projections using 3-D distance maps, in Laugier C. (eds): Geometric Reasoning for Perception and Action. GRPA 1991, Lecture Notes in Computer Science, vol. 708. Springer, Berlin, Heidelberg. In this approach, additional effects such as image distortion (e.g., a pillow effect introduced by an image intensifier) or the bending of a nail may be accounted for by introducing additional degrees of freedom into the parameter vector or by using a suitably adjusted model.

According to an embodiment, for objects described by a statistical shape or appearance model, the matching of virtual projection to the actual projection may proceed along the lines of V. Blanz, T. Vetter (2003), Face Recognition Based on Fitting a 3D Morphable Model, IEEE Transactions on Pattern Analysis and Machine Intelligence. In this paper, a statistical, morphable 3D model is fitted to 2D images. For this, statistical model parameters for contour and appearance and camera and pose parameters for perspective projection are determined. Another approach may be to follow X. Dong and G. Zheng, Automatic Extraction of Proximal Femur Contours from Calibrated X-Ray Images Using 3D Statistical Models, in T. Dohi et al. (Eds.), Lecture Notes in Computer Science, 2008. Deforming a 3D model in such a way that its virtual projection matches the actual projection of the object in the X-ray image also allows a computation of an imaging direction (which describes the direction in which the X-ray beam passes through the object).

When displaying the X-ray image, geometrical aspects and/or dimensions may be shown as an overlay in the projection image. Alternatively, or additionally, at least a portion of the model may be shown in the projection image, for example as a transparent visualization or 3D rendering, which may facilitate an identification of structural aspects of the model and thus of the imaged object by a user.

General Comments

For the definition of a C-arm's rotation and translation axes, it is referred to FIG. 25. In this figure, the X-ray source is denoted by XR, the rotation axis denoted by the letter B is called the vertical axis, the rotation axis denoted by the letter D is called the propeller axis, and the rotation axis denoted by the letter E will be called the C-axis. It is noted that for some C-arm models, the axis E may be closer to axis B. The intersection between axis D and the central X-ray beam (labeled with XB) is called the center of the C-arm's "C". The C-arm may be moved up and down along the direction indicated by the letter A. The C-arm may also be moved along the direction indicated by the letter C. The distance of the vertical axis from the center of the C-arm's "C" may differ between C-arms. It is noted that it may also be possible to use a G-arm instead of a C-arm.

A neural net may be trained based on a multiplicity of data that is comparable to the data on which it will be applied. In case of an assessment of bone structures in images, a neural net should be trained on the basis of a multiplicity of X-ray images of bones of interest. It will be understood that the neural net may also be trained on the basis of simulated X-ray images.

According to an embodiment, more than one neural network may be used, wherein each of the neural nets may specifically be trained for a sub-step necessary to achieve a desired solution. For example, a first neural net may be trained to evaluate X-ray image data so as to classify an anatomical structure in the 2D projection image, whereas a second neural net may be trained to detect characteristic edges of that structure in the 2D projection image. A third net may be trained to determine specific key points like the center of a femoral head. It is also possible to combine neural networks with other algorithms, including but not limited to, model-based algorithms like Active Shape Models. It is noted that a neural net may also directly solve one of the tasks in this invention, e.g., a determination of an implantation curve.

It is noted that a processing unit may be realized by only one processor performing all the steps of the process, or by a group or a plurality of processors, which need not be located at the same place. For example, cloud computing allows a processor to be placed anywhere. For example, a processing unit may be divided into a first sub-processor that controls interactions with the user, including a monitor for visualizing results, and a second sub-processor (possibly located elsewhere) that performs all computations. The first sub-processor or another sub-processor may also control movements of, for example, a C-arm or a G-arm of an X-ray imaging device.

According to an embodiment, the device may further comprise storage means providing a database for storing, for example, X-ray images. It will be understood that such storage means may also be provided in a network to which the system may be connected, and that data related to a neural net may be received over that network. Furthermore, the device may comprise an imaging unit for generating at least one 2D X-ray image, wherein the imaging unit may be capable of generating images from different directions.

According to an embodiment, the system may comprise a device for providing information to a user, wherein the information includes at least one piece of information out of the group consisting of X-ray images and instructions regarding step of a procedure. It will be understood that such a device may be a monitor or an augmented reality device for visualization of the information, or it may be a loud-speaker for providing the information acoustically. The device may further comprise input means for manually determining or selecting a position or part of an object in the X-ray image, such as a bone outline, for example for measuring a distance in the image. Such input means may be for example a computer keyboard, a computer mouse or a touch screen, to control a pointing device like a cursor on a monitor screen, which may be included in the device. The device may also comprise a camera or a scanner to read the labeling of a packaging or otherwise identify an implant or surgical tool. A camera may also enable the user to communicate with the device visually by gestures or mimics, e.g., by virtually touching devices displayed by virtual reality. The device may also comprise a microphone and/or loudspeaker and communicate with the user acoustically.

It is noted that all references to C-arm movements in this disclosure always refer to a relative repositioning between C-arm and patient. Hence, any C-arm translation or rotation may in general be replaced by a corresponding translation or rotation of the patient/OR table, or a combination of C-arm translation/rotation and patient/table translation/rotation. This may be particularly relevant when dealing with extremities since in practice moving the patient's extremities may be easier than moving the C-arm. It is noted that the required patient movements are generally different from the C-arm movements, in particular, typically no translation of the patient is necessary if the target structure is already at the desired position in the X-ray image. The system may compute C-arm adjustments and/or patient adjustments. It is furthermore noted that all references to a C-arm may analogously apply to a G-arm.

The methods and techniques disclosed in this invention may be used in a system that supports a human user or surgeon, or they may also be used in a system where some or all of the steps are performed by a robot. Hence, all references to a "user" or "surgeon" in this patent application may refer to a human user as well as a robotic surgeon, a mechanical support device, or a similar apparatus. Similarly, whenever it is mentioned that instructions are given how to adjust the C-arm, it is understood that such adjustments may also be performed without human intervention, i.e., automatically, by a robotic C-arm, by a robotic table, or they may be performed by OR staff with some automatic support. It is noted that because a robotic surgeon and/or a robotic C-arm may operate with higher accuracy than humans, iterative procedures may require fewer iterations, and more complicated instructions (e.g., combining multiple iteration steps) may be executed.

A computer program may preferably be loaded into the random-access memory of a data processor. The data processor or processing unit of a system according to an embodiment may thus be equipped to carry out at least a part of the described process. Further, the invention relates to a computer-readable medium such as a CD-ROM on which the disclosed computer program may be stored. However, the computer program may also be presented over a network like the World Wide Web and can be downloaded into the random-access memory of the data processor from such a network. Furthermore, the computer program may also be executed on a cloud-based processor, with results presented over the network.

It is noted that prior information about an implant (e.g., the size and type of a nail) may be obtained by simply scanning the implant's packaging (e.g., the barcode) or any writing on the implant itself, before or during surgery.

As should be clear from the above description, a main aspect of the invention is a processing of X-ray image data, allowing an automatic interpretation of visible objects. The methods described herein are to be understood as methods assisting in a surgical treatment of a patient. Consequently, the method may not include any step of treatment of an animal or human body by surgery, in accordance with an embodiment.

It will be understood that steps of methods described herein, and in particular of methods described in connection with workflows according to embodiments some of which are visualized in the figures, are major steps, wherein these major steps might be differentiated or divided into several sub-steps. Furthermore, additional sub-steps might be between these major steps. It will also be understood that only part of the whole method may constitute the invention, i.e. steps may be omitted or summarized.

It has to be noted that embodiments are described with reference to different subject-matters. In particular, some embodiments are described with reference to method-type claims (computer program) whereas other embodiments are described with reference to apparatus-type claims (system/device). However, a person skilled in the art will gather from the above and the following description that, unless otherwise specified, any combination of features belonging to one type of subject-matter as well as any combination between features relating to different subject-matters is considered to be disclosed with this application.

The aspects defined above and further aspects, features and advantages of the present invention can also be derived from the examples of the embodiments to be described hereinafter and are explained with reference to examples of embodiments also shown in the figures, but to which the invention is not limited.

BRIEF DESCRIPTION OF THE DRAWINGS

The present invention will hereinafter be described in conjunction with the following drawing figures, wherein like numerals denote like elements, and.

Figure 1:
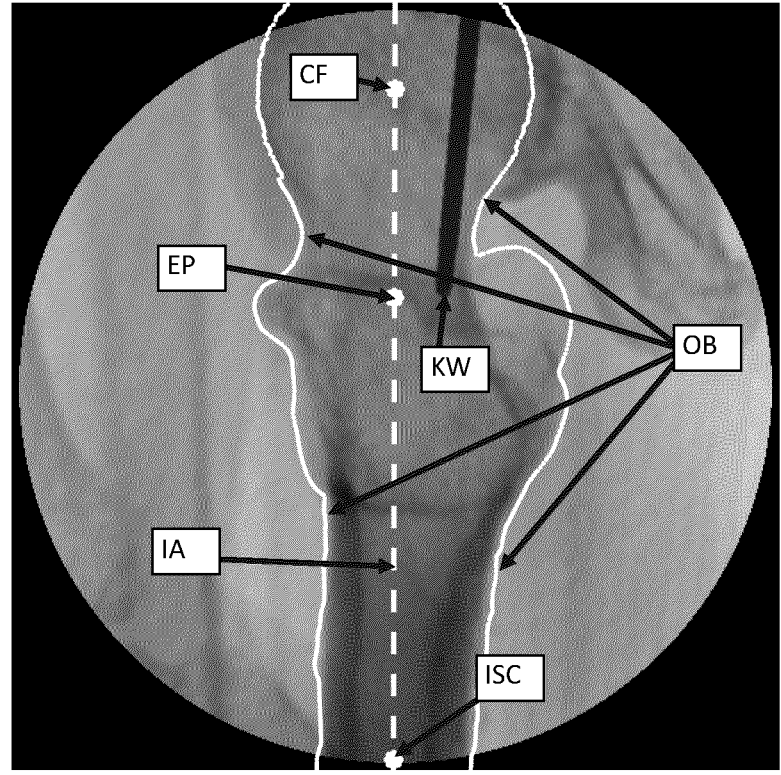
FIG. 1 shows a lateral X-ray image of a femur for determining the entry point of an intramedullary nail.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION OF THE
EMBODIMENTS

The following detailed description is merely exemplary in nature and is not intended to limit the invention or the application and uses of the invention. Furthermore, there is no intention to be bound by any theory presented in the preceding background of the invention or the following detailed description.

Determining an Entry Point for Implanting an Intramedullary Nail into a Femur

A first aim of this invention may be a determination of an implantation curve and an entry point for implanting an intramedullary nail into a femur. For determining the entry point, an X-ray image needs to be acquired from a certain viewing direction. In a true lateral view, the shaft axis and the neck axis are parallel with a certain offset. However, this view is not the desired view of this invention. The desired view is a lateral view with a rotation around the C-axis of the C-arm such that the implantation axis will run through the center of the femoral head. The center of the femoral head may, for instance, be determined by a neural network with a sufficiently high accuracy. Uncertainty in determining the center of the femoral head may mainly concern a deviation in the direction of the implantation axis, which does not significantly affect the accuracy of ensuring the desired viewing direction. The system may support the user in obtaining the desired viewing direction by estimating the needed rotation angle around the C-axis based on an anatomy database or based on LU100907B1.

Figure 25:
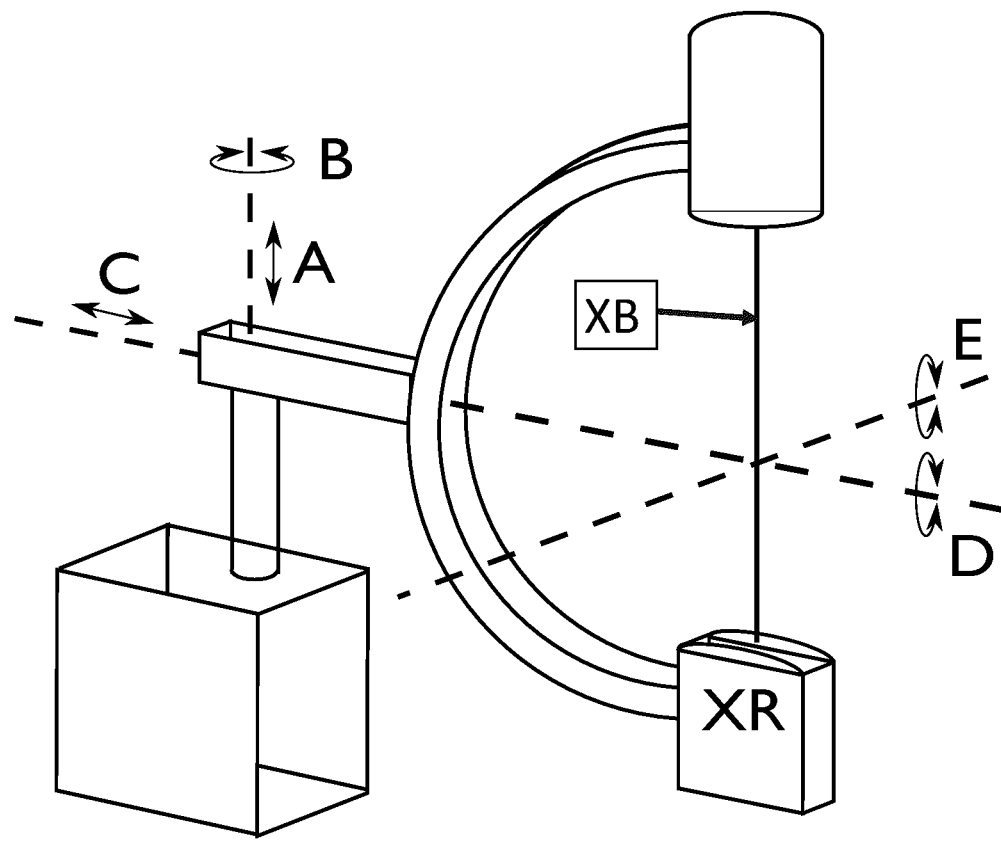
FIG. 25 shows a C-arm with its rotation and translation axes.

The system may also help the user obtain the correct viewing direction. For instance, consider the scenario where the 2D distance between the center of the femoral head and the tip of an opening instrument is too small compared to the 2D distance between the tip of the opening instrument and the lowest visible part of the femoral shaft. This effect occurs when the focal axis of the C-arm is almost perpendicular to the implantation axis. If this is the case, the center of the shaft at the isthmus will most likely not be visible in the current X-ray projection image. Hence, the system may give an instruction to rotate the C-arm around axis B in FIG. 25. Following the instruction will lead to an X-ray projection image where the first distance is increased and the second distance is decreased (i.e., the neck region is larger, and the isthmus of the shaft becomes visible).

A method to determine by which angle the C-arm needs to be rotated in order to obtain the desired view as described above may be to consider the anatomical appearance in the AP X-ray image. The following points may be identified in the image: the center of the femoral head, the tip of an opening instrument, and the center of the shaft at the transition to the greater trochanter. Two lines may then be drawn between the first two points and the latter two points, respectively. Since these three points may also be identified in an ML X-ray image with a sufficient accuracy, it may be possible to estimate the angle between the focal line of the ML X-ray image and the anatomy (e.g., the implantation axis and/or the neck axis). If this angle is too small or too large, the system may give an instruction that will increase or decrease the angle, respectively.

According to an embodiment, the implantation axis may be determined as follows. FIG. 1 shows a lateral (ML) X-ray image of a femur. The system may detect the center of the shaft at the isthmus (labeled ISC) and the center of the femoral head (labeled CF). The line defined by these two points may be assumed to be the implantation axis (labeled IA). Furthermore, the system may detect the projected outer boundaries (labeled OB) of the neck region and the shaft region, or alternatively a plurality of points on the boundaries. The segmentation of the boundaries may be done, for instance, by a neural network. Alternatively, a neural network may directly estimate specific points instead of the complete boundary. For instance, instead of the boundaries of the shaft, the neural network might estimate the center of the shaft, and the shaft diameter may be estimated based on the size of the femoral head. Based on this information it may be possible to estimate the location of the shaft boundary without finding the boundary itself. The implantation axis should have a certain distance from both the neck boundary and the shaft boundary. If either distance is too small, the system may calculate the needed rotation around the C-axis of the C-arm such that the desired viewing direction is reached in a subsequently acquired X-ray projection image. The direction of the C-arm rotation may be determined based on a weighted evaluation of the distance in the neck region and the distance in the shaft region. The angle of the rotation may be calculated based on an anatomical model of the femur.

Once the desired viewing direction is reached, the intersection of the implantation axis with the trochanter rim axis may be defined as the entry point. The trochanter rim axis may be detected directly in the image. If this is not desired or feasible, the trochanter rim axis may also be approximated in the X-ray image by a line connecting the tip of an opening instrument with the implantation axis. This line may be assumed to be perpendicular to the implantation axis, or if available a priori information suggests otherwise, it may run at an oblique angle to the implantation axis.

The implant may consist of a nail and a head element. If the distance between the projected tip of the opening instrument and the projected entry point is not within a desired distance (e.g., the distance is larger than 1 mm), the system may guide the user how to move the opening instrument in order to reach the entry point. For instance, if the tip of the opening instrument on a femur is positioned too anterior compared to the determined entry point, the system gives an instruction to move the tip of the opening instrument in a posterior direction.

According to an embodiment, the system may detect the isthmus of the femoral shaft, the center of the femoral head (labeled CF), and the tip of an opening instrument in the X-ray (labeled KW). The implantation axis (labeled IA) may be assumed to be the line running through the center of the femoral head (labeled CF) and the center at the isthmus of the shaft (labeled ISC). The entry point may be assumed to be the point (labeled EP) on the implantation axis that is closest to the tip of the opening instrument KW. The system may give an instruction to move the opening instrument so that it is placed on EP. After moving the instrument to the projected point, it may be helpful to acquire an AP image in order to verify that the tip of the opening instrument is still on the projected tip of the greater trochanter in the AP view. In case that there is knowledge about a projected epipolar line from the detected K-Wire tip in AP image possibly based on a registration of the AP image with the ML image, and there has been no movement of the k-wire tip in between acquisition of AP image and acquisition of the ML image this would result in a more accurate determination of the entry point where no additional verification in another AP image whether the tip is still positioned on the projected tip of the greater trochanter might be necessary.

Figure 33:
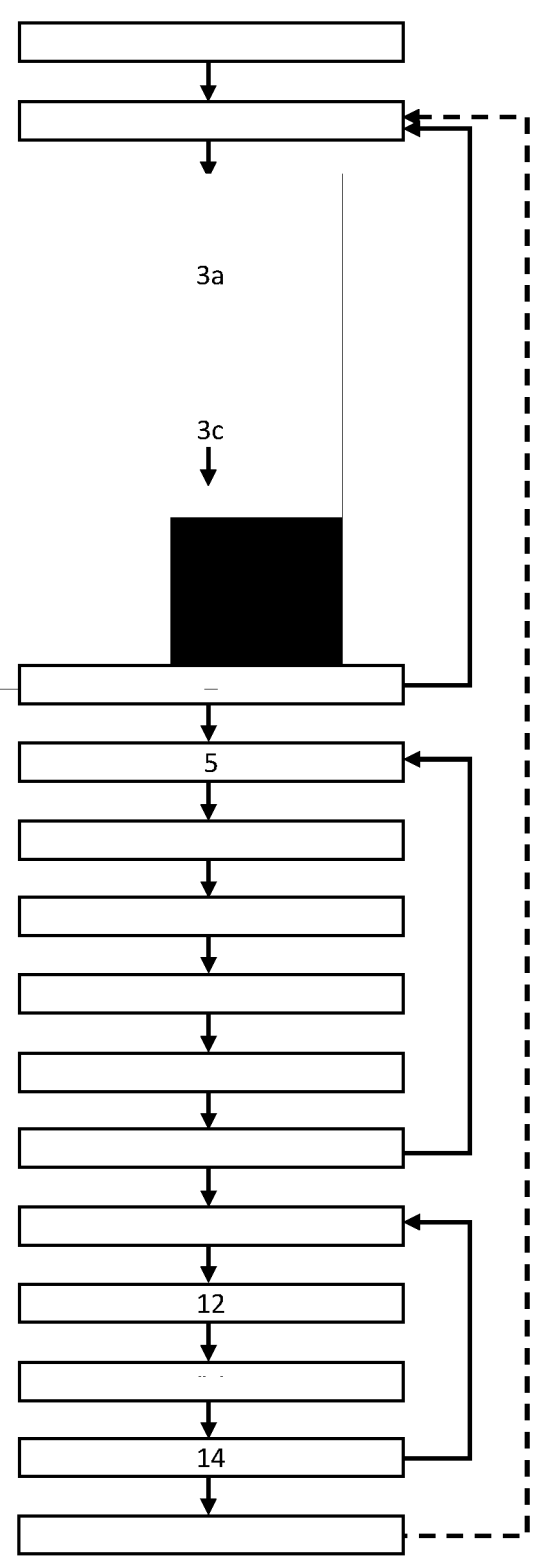
FIG. 33 shows a potential workflow for determining the entry point for an intramedullary implant in a femur.

Example for a Potential Workflow for Determining the Entry Point for an Intramedullary Implant in the Femur (Cf. FIG. 33)

1. The user acquires an AP X-ray image, in which the tip of an opening instrument is placed on the projected tip of the greater trochanter.
2. Without moving the tip of the opening instrument, the user acquires an ML X-ray projection image.
3. The system detects the center of the femoral head, the center point of the isthmus of the shaft, and the tip of the opening instrument in the X-ray image.
   a. If both the femoral head and the shaft isthmus are not sufficiently visible, the system gives an instruction to move the C-arm in lateral direction to increase the field of view.
   b. If only the femoral head is not sufficiently visible whereas the isthmus is fully visible, the system gives an instruction to move the C-arm in proximal direction along the leg.
   c. The system calculates a first distance between the center of the femoral head and the tip of the opening instrument, and a second distance between the tip of the opening instrument and a certain point of the shaft. This point might be the center of the shaft at the isthmus (if it is visible), or, if the isthmus is not visible, the most distal visible point of the shaft or alternatively, the estimated center of the shaft at the isthmus (based on the visible part of the shaft).
   d. If only the shaft is not sufficiently visible, whereas the femoral head is completely visible, the system gives an instruction to move the C-arm in distal direction along the leg. One method to determine whether the shaft is sufficiently visible may be to compare the second distance from step 3c with a threshold. Another method may be to evaluate the curvature of the shaft in order to determine whether the isthmus is visible in the current X-ray image.
   e. If the first distance from step 3c is too small compared to the second distance, the C-arm needs to be rotated clockwise (right femur) or counter-clockwise (left femur) around C-arm axis B (cf. FIG. 25), and vice versa. The angle by which the C-arm needs to be rotated may be calculated based on the two distances and possibly additional information from the AP image from step 1. The latter may include, for instance, the CCD angle of the femur. The curvature of the shaft as depicted in the ML X-ray image may also be taken into account.

4. Steps 2 and 3 are repeated until all important parts of the femur are sufficiently visible and the two distances from step 3c have the desired ratio.
5. In addition to the points from step 3, the system detects the left and right outlines of the femoral neck and the left and right outlines of the femoral shaft.
6. A line is drawn from the center of the femoral head to the center at the isthmus of the shaft. Four distances are calculated between this line and the four outlines of the femoral neck and the femoral shaft.
7. For each the neck and the shaft region, a metric is defined to evaluate how central the line runs through each of the regions. Example: The metric for the neck is 0 when the line touches the left outline of the neck, and it is 1 when the line touches the right outline of the femur; it is 0.5 when the line is located in the center of the neck region.
8. A new metric is defined based on a weighted mean of the neck metric and the shaft metric. If the new metric is lower than a first threshold, the C-arm needs to be rotated around its C-axis such that the focal point of the C-arm moves in anterior direction. If the new metric is higher than a second threshold, which is higher than the first threshold, the C-arm needs to be rotated around its C-axis in the opposite direction. The angle by which the C-arm needs to be rotated may be calculated based on the distance between the metric and the corresponding threshold.
9. If the metric defined in step 8 is outside the two thresholds from step 8, a new ML X-ray projection image must be acquired.
10. Steps 5 to 9 are repeated until the metric defined in step 8 is between the two thresholds from step 8. The drawn line is the final projected implantation axis.
11. The distance between the projected tip of the opening instrument and the line from step 10 is calculated.
12. Optional: The tip of the opening instrument is localized. Based on the appearance of the tip of the opening instrument (i.e., its size in the X-ray projection image), the system gives an instruction for moving the tip of the opening instrument either in posterior or anterior direction.
13. If the tip of the opening instrument is too far from the line from step 10, its position is optimized and a new ML X-ray projection image is acquired.
14. Steps 11 to 13 are repeated until the tip of the opening instrument is within a certain distance to the line from step 10.
15. An AP X-ray projection image is acquired to ensure that the tip of the opening instrument is still on the tip of the greater trochanter. If this is not the case, return to step 2.

Procedure for Implanting a Nail with Sub-Implants into a Tibia

Figure 26:
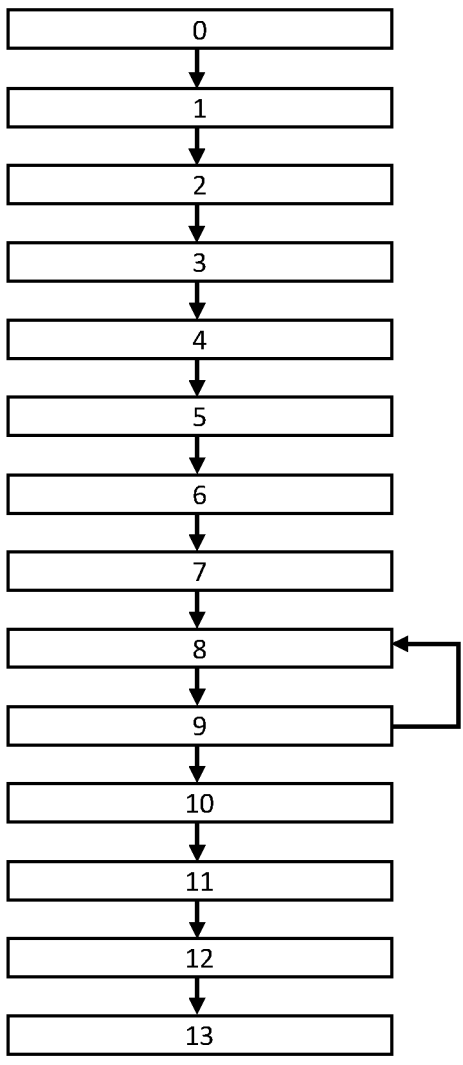
FIG. 26 shows a potential workflow for determining an entry point for a tibia.

Example for a Potential Workflow (Cf. FIG. 26)

Figure 2:
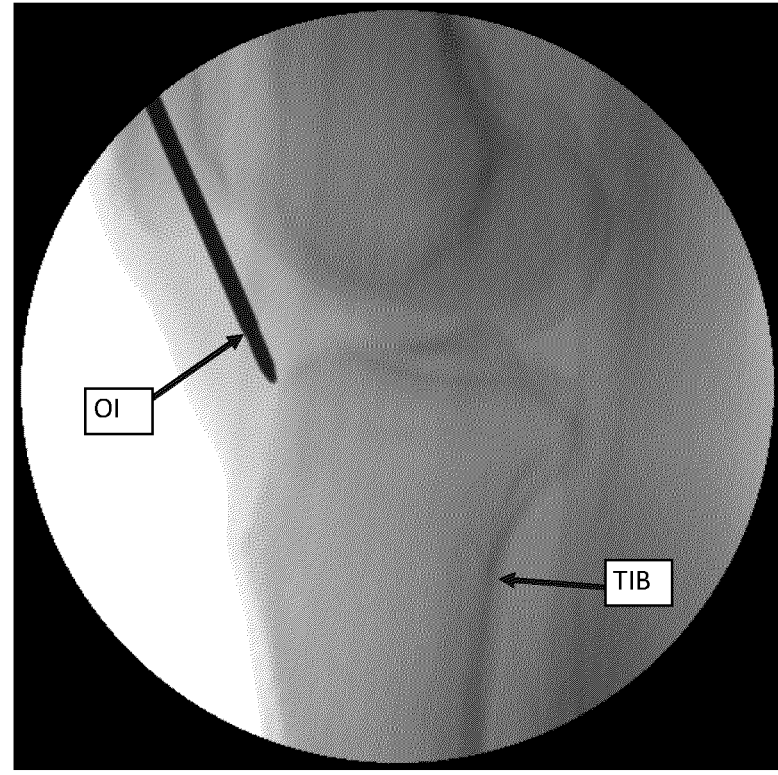
FIG. 2 shows an ML X-ray image of the proximal part of a tibia and an opening instrument.

0. For the following workflow it is assumed that the proximal part of the tibia is intact (or correctly repositioned).
1. The user places an opening instrument onto the surface of the tibia (at an arbitrary point of the proximal part, but ideally in the vicinity of an entry point as estimated by the surgeon).
2. The user acquires an (approximately) lateral image of the proximal part of the tibia (labeled TIB) as depicted in FIG. 2.

Figure 3:
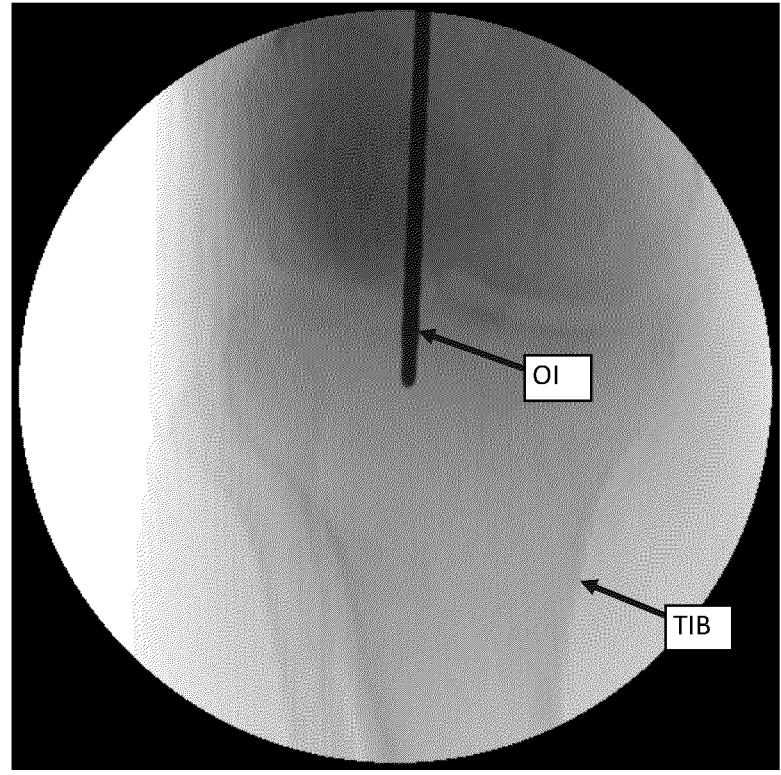
FIG. 3 shows an AP X-ray image of the proximal part of a tibia and an opening instrument.
Figure 4:
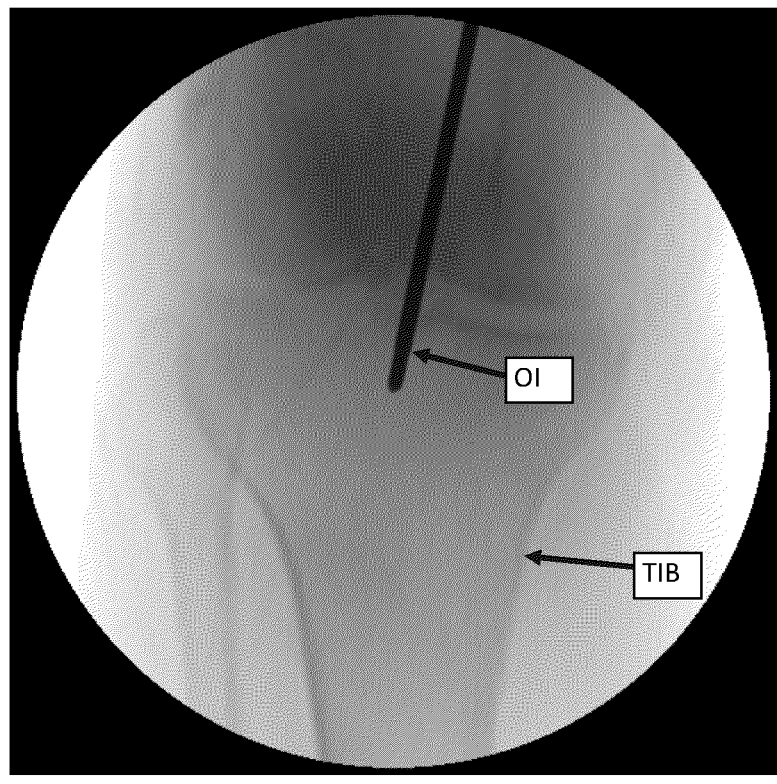
FIG. 4 shows an AP X-ray image of the proximal part of a tibia and an opening instrument.
Figure 5:
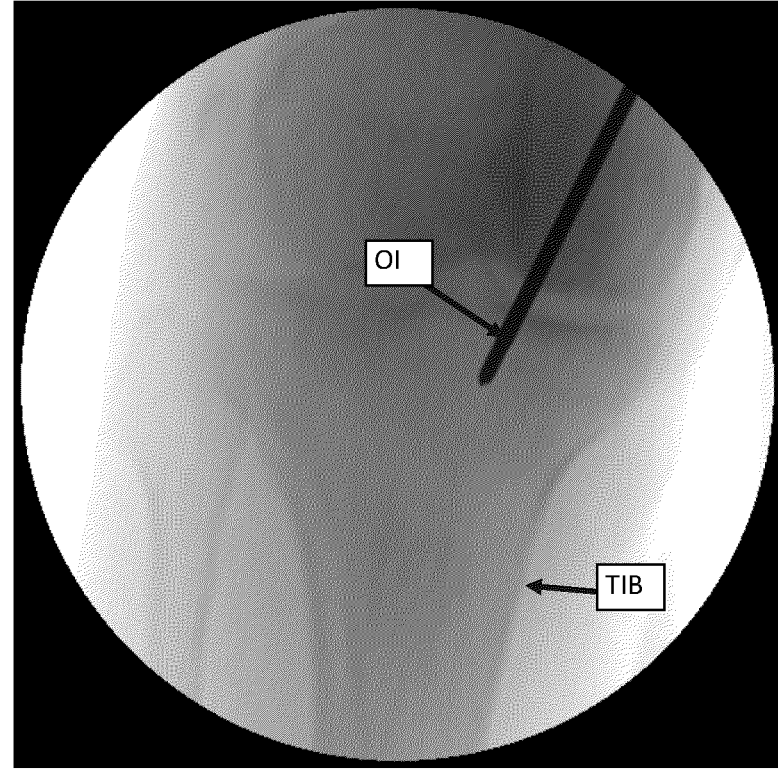
FIG. 5 shows an AP X-ray image of the proximal part of a tibia and an opening instrument.
Figure 6:
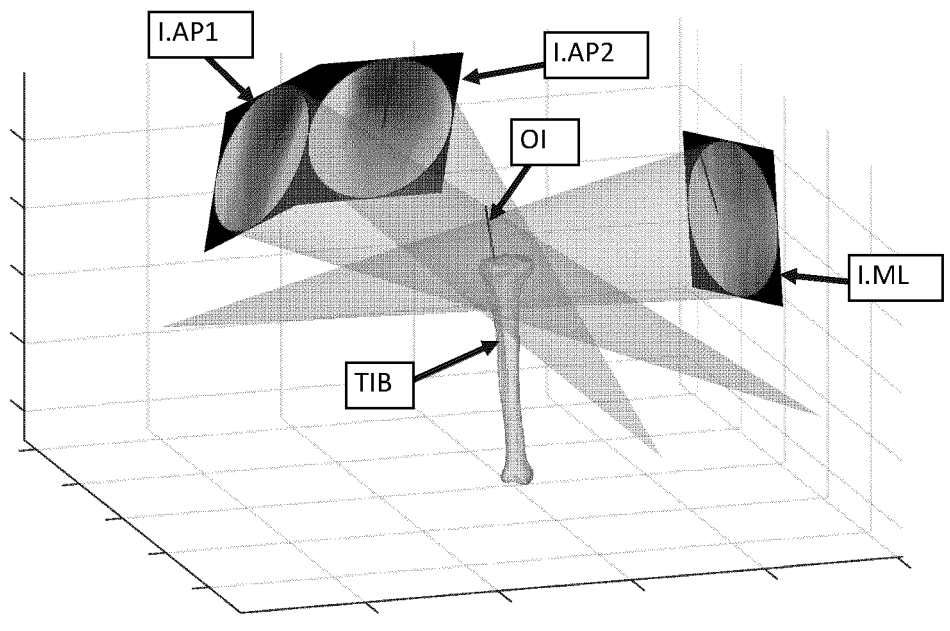
FIG. 6 shows an image registration for a tibia based on two AP X-ray images and one ML X-ray image.

3. The user acquires at least one AP image (ideally, multiple images from slightly different directions) of the proximal part of the tibia as depicted in FIG. 3, FIG. 4, and FIG. 5.
4. The system detects the size (or diameter, etc.) of the opening instrument (labeled OI) in all images in order to estimate the size (scaling) of the tibia.
5. The system jointly matches a statistical model of the tibia into all images, e.g., by matching the statistical model to the bone contours (or, more generally, the appearance of the bone). The result of this step is a 3D reconstruction of the tibia.
   a. This includes six parameters per image for rotation and translation, one parameter for the scaling (which was already initially estimated in step 4), and a certain number of modes (determining the modes is equivalent to a 3D reconstruction of the tibia). Hence, if there are n images and m modes, the total number of parameters is $(6 \cdot n+1+m)$.
   b. Based on all estimated rotations and translations of the tibia (in each image), the system performs an image registration for all images as depicted in FIG. 6. Hence, the spatial relation between the AP images (labeled I.AP1 and I.AP2), the ML image (labeled I.ML), the tip of the opening instrument (labeled OI), and the tibia (labeled TIB) is known.
   c. Optional: For a potentially more accurate result, the system may use information of the femoral condyles or the fibula, e.g., by using statistical information for these bones.
6. Based on the 3D reconstruction of the tibia, the system determines an entry point. This may be done, for instance, by defining the entry point on the mean shape of the statistical model. This point may then be identified on the 3D reconstruction.
7. Optional: Based on the 3D reconstruction of the tibia, the system places the implant into the bone (virtually) and calculates the length of the proximal locking screws. This step may also improve the estimation of the entry point since it considers the actual implant.
8. The system displays the entry point as an overlay in the current X-ray image.
9. If the tip of the opening instrument is not close enough to the estimated entry point, the system gives an instruction to correct the position of the tip.
   a. The user corrects the position of the tip of the opening instrument and acquires a new X-ray image.
   b. The system calculates the entry point in the new image (e.g., by image difference analysis or by matching the 3D reconstruction of the tibia into the new image).
   c. Return to step 8.
10. The user inserts the implant into the tibia and acquires a new image.
11. The system localizes the implant. Based on the 3D reconstruction of the tibia, the system provides necessary 3D information (e.g., the length of the proximal locking screws).
12. The system provides support for proximal locking.
13. The system calculates the torsion angle by comparing the proximal part of the tibia (this may include the femoral condyles) and the distal part of the tibia (this may include the foot). For a more accurate calculation of the torsion angle, the system may also use information about the fibula (e.g., by localizing the fibula and calculating its spatial relation to the tibia).

Procedure for Implanting a Nail with Sub-Implants into a Humerus

Figure 27:
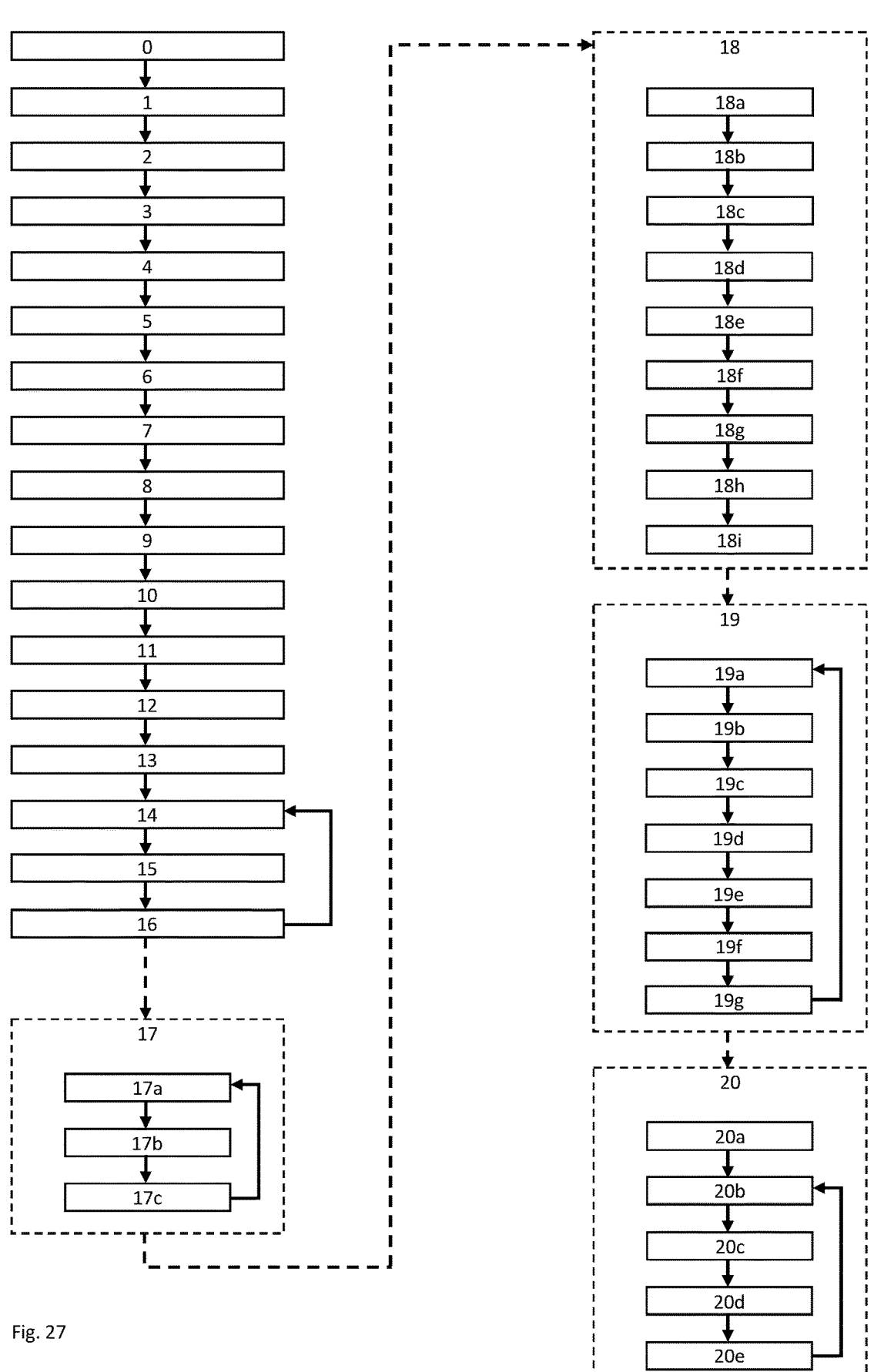
FIG. 27 shows a potential workflow for determining an entry point for a humerus.

Example for a Potential Workflow (Cf. FIG. 27)

Figure 7:
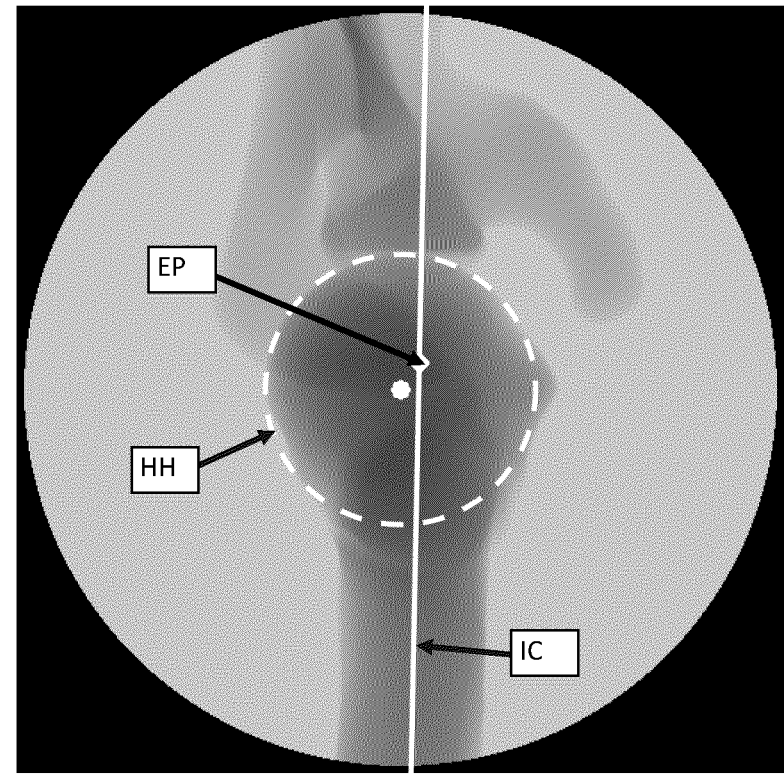
FIG. 7 shows an axial X-ray image of the proximal part of a humerus.
Figure 8:
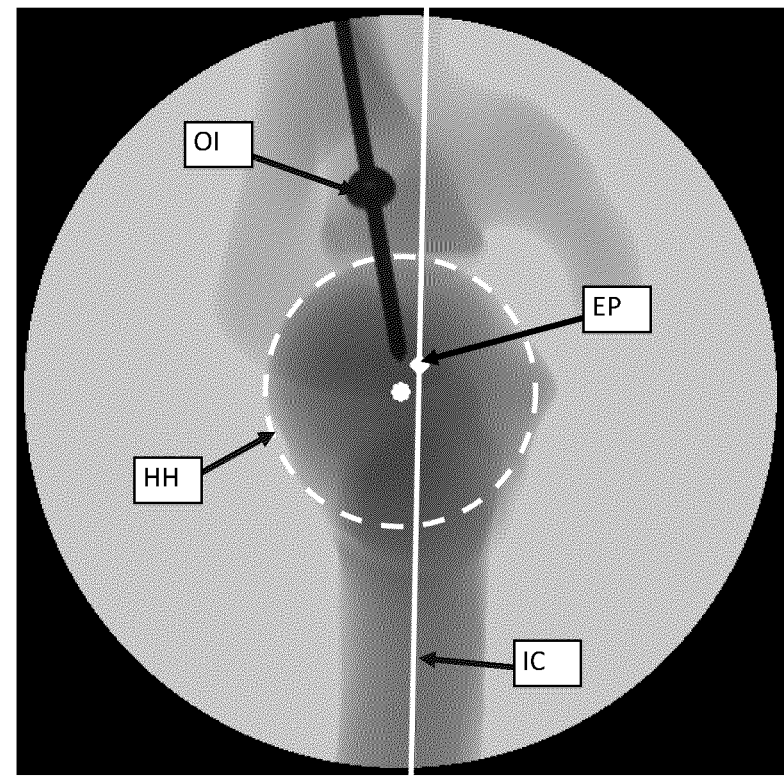
FIG. 8 shows an axial X-ray image of the proximal part of a humerus and a guide rod.
Figure 9:
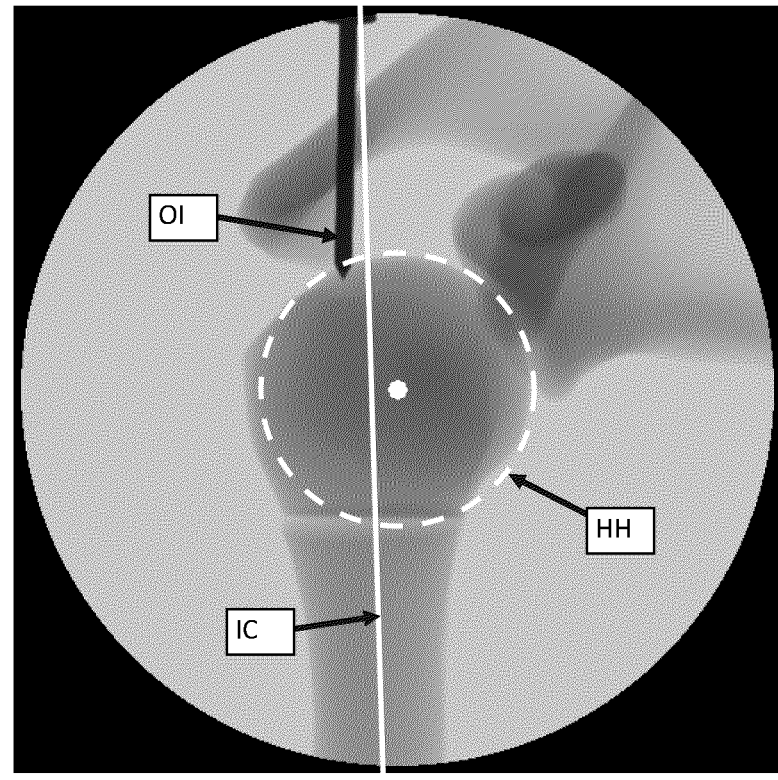
FIG. 9 shows an AP X-ray image of the proximal part of a humerus and a guide rod.
Figure 10:
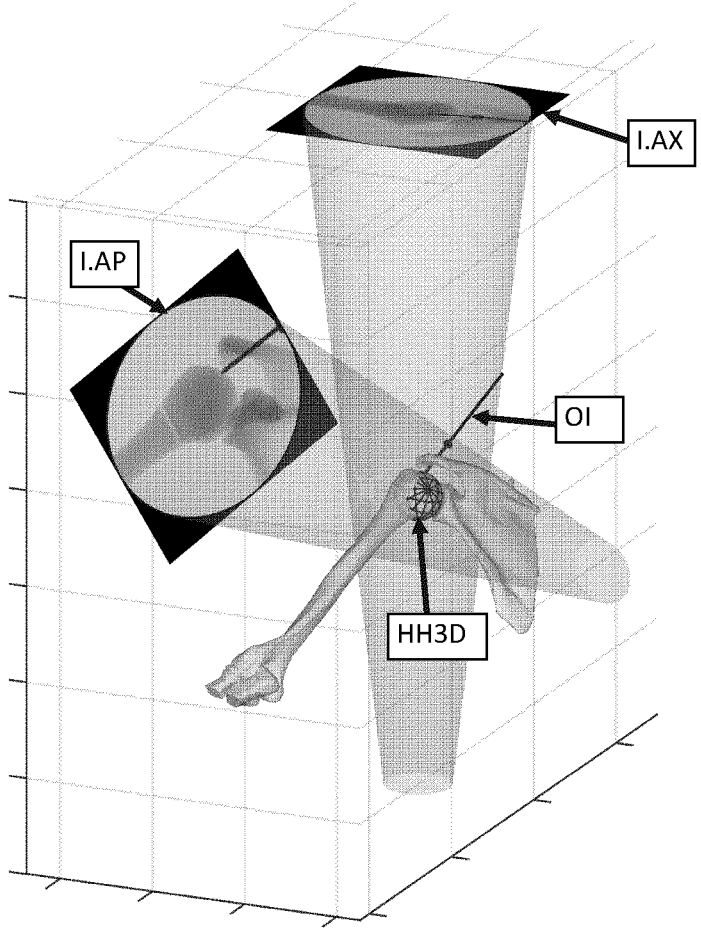
FIG. 10 shows an image registration for a humerus based on an AP X-ray image and an axial X-ray image.
Figure 11:
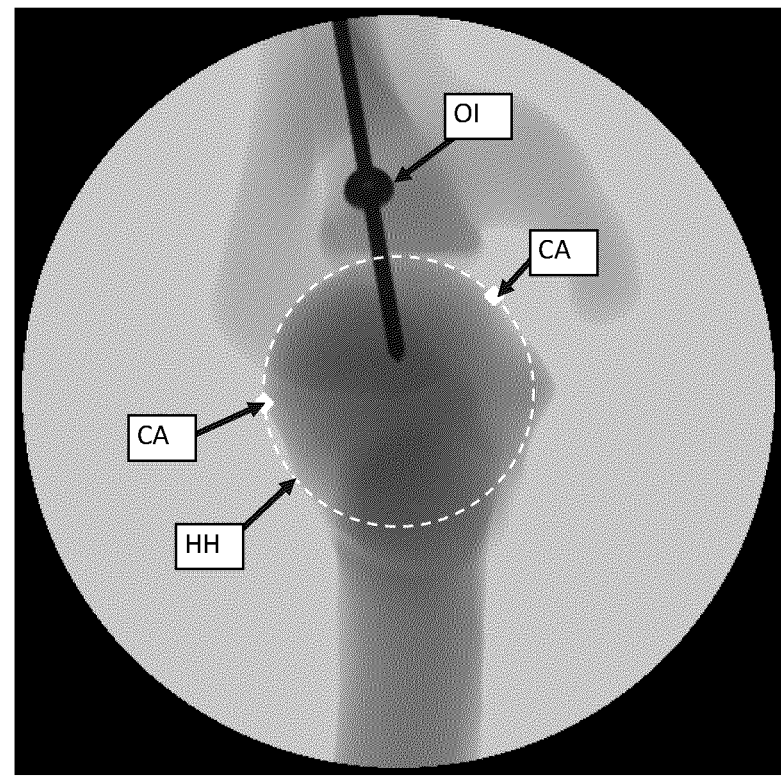
FIG. 11 shows an axial X-ray image of the proximal part of a humerus, 2D points of the collum anatomicum, and a guide rod.
Figure 12:
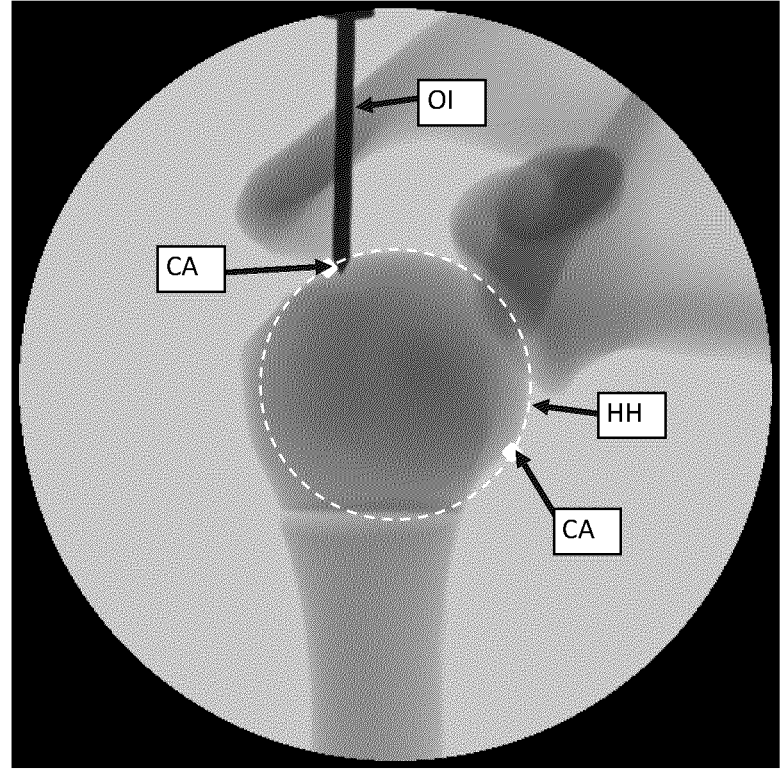
FIG. 12 shows an AP X-ray image of the proximal part of a humerus, 2D points of the collum anatomicum, and a guide rod.
Figure 13:
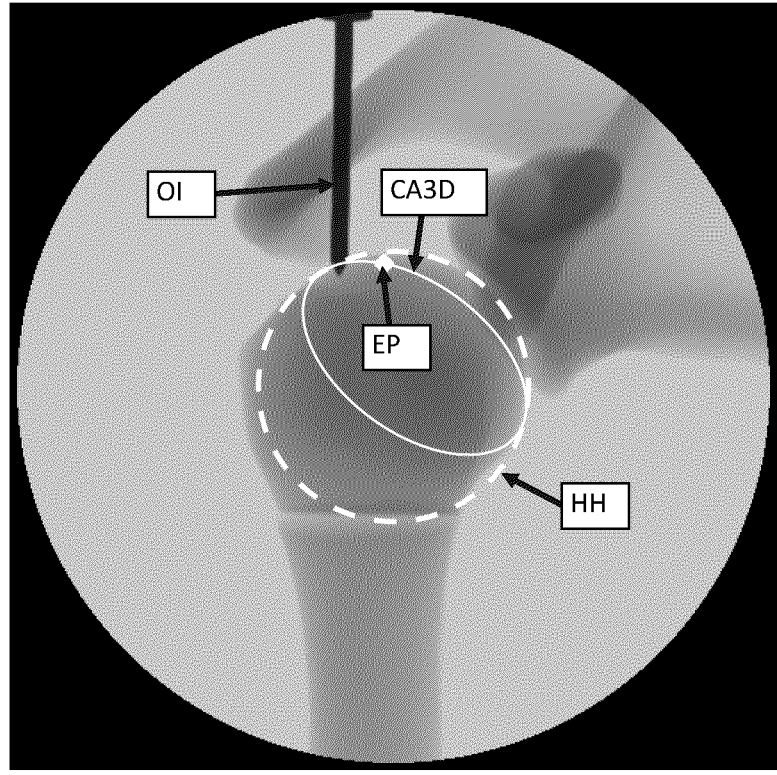
FIG. 13 shows an AP X-ray image of the proximal part of a humerus, the 2D projected collum anatomicum, the entry point, and a guide rod.
Figure 14:
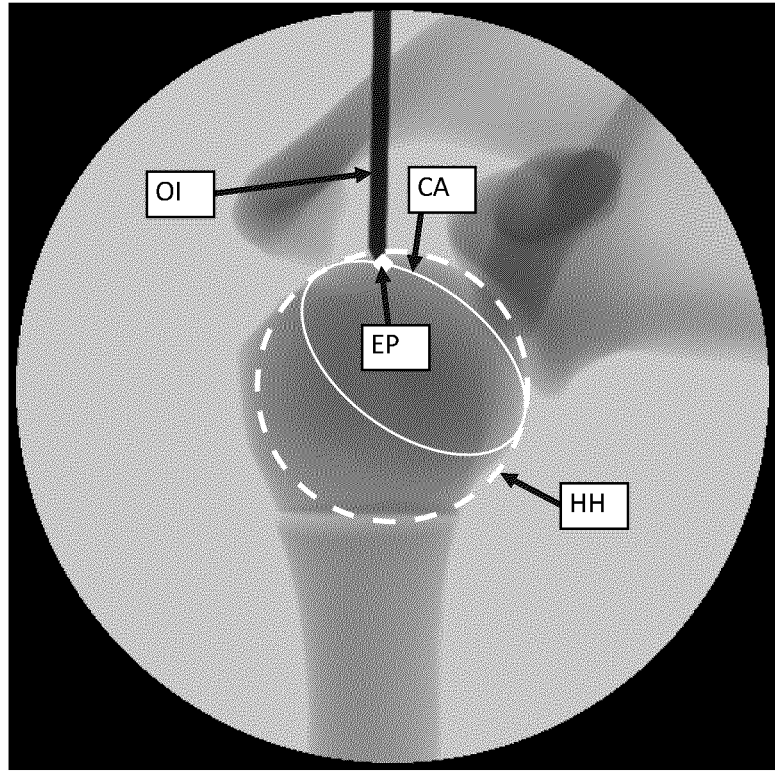
FIG. 14 shows an AP X-ray image of the proximal part of a humerus, the 2D projected collum anatomicum, the entry point, and a guide rod with its tip on the entry point.
Figure 15:
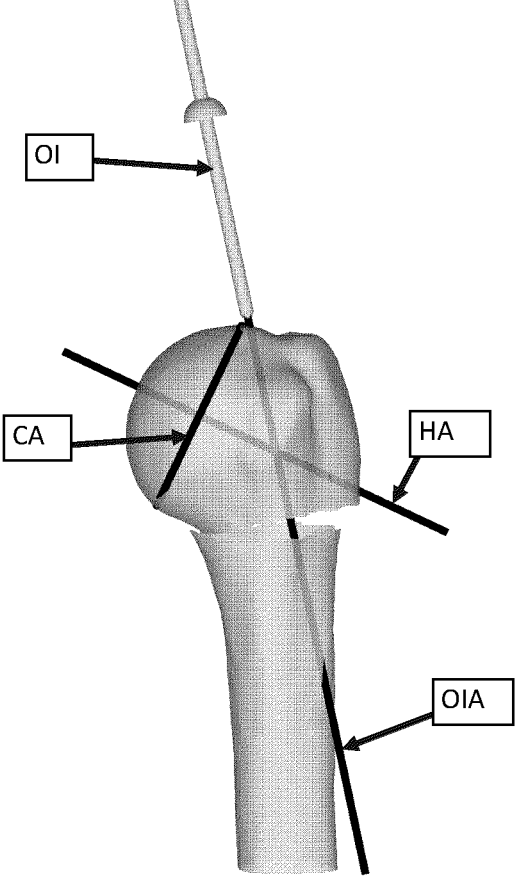
FIG. 15 shows a fractured 3D humerus and a guide rod from an AP viewing direction.
Figure 16:
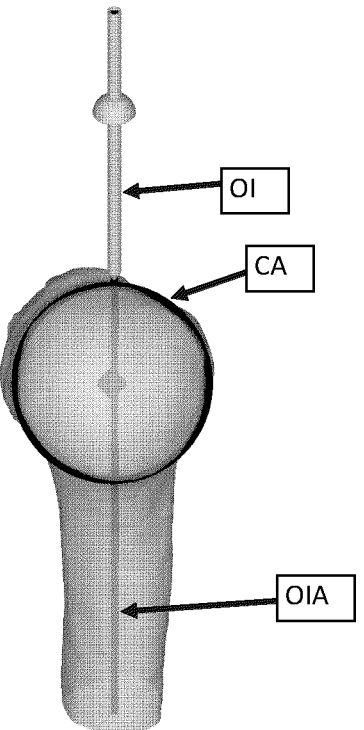
FIG. 16 shows a fractured 3D humerus and a guide rod from an axial viewing direction.
Figure 17:
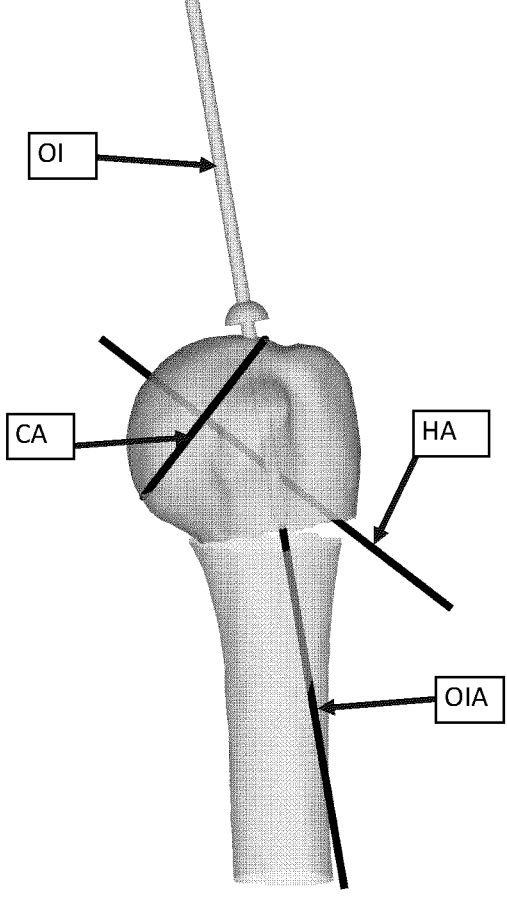
FIG. 17 shows a fractured 3D humerus and an inserted guide rod from an AP viewing direction.
Figure 18:
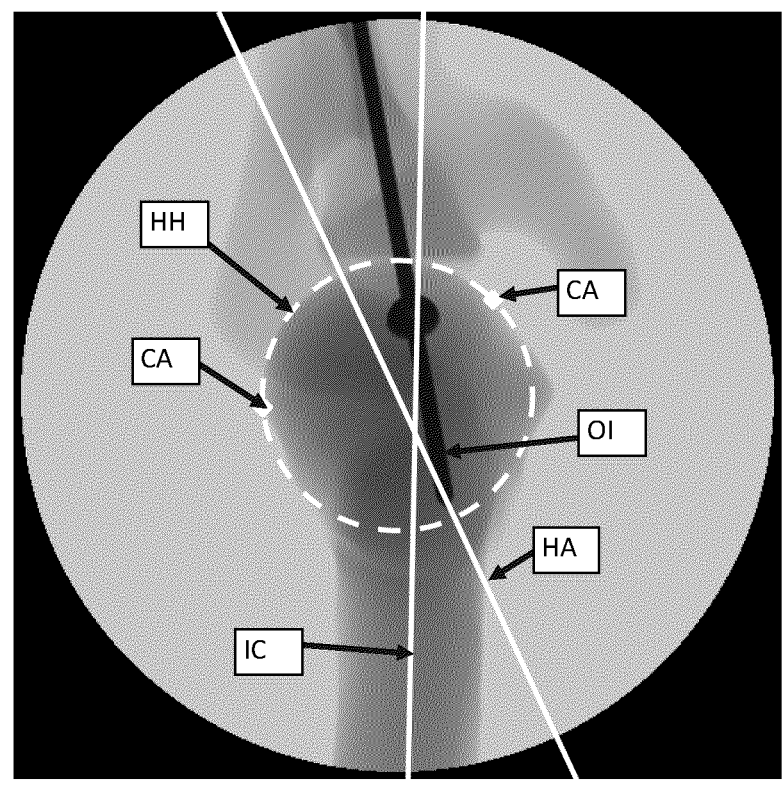
FIG. 18 shows an axial X-ray image of the proximal part of a humerus, 2D points of the collum anatomicum, and an inserted guide rod.
Figure 19:
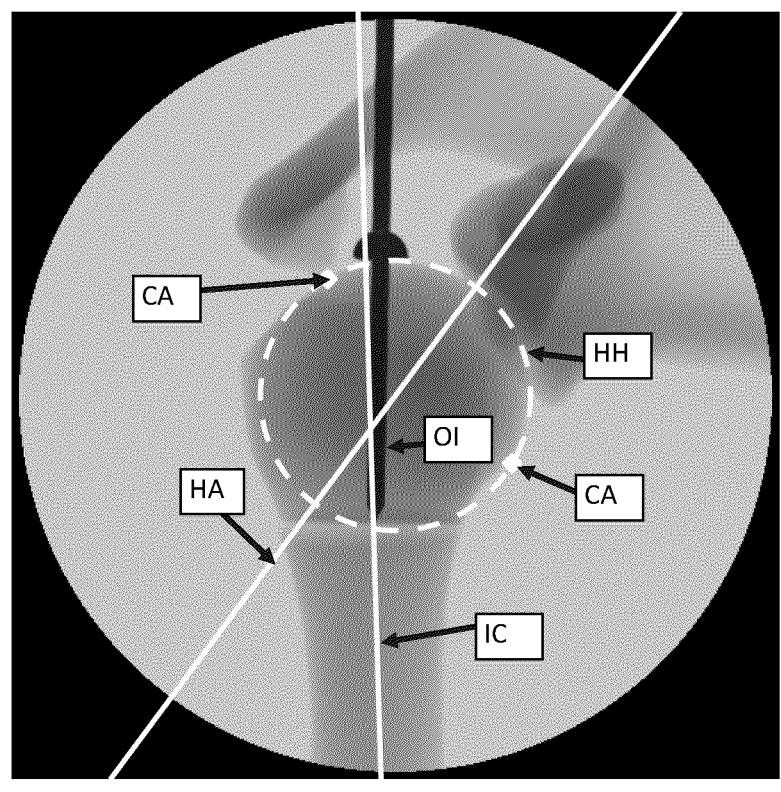
FIG. 19 shows an AP X-ray image of the proximal part of a humerus, 2D points of the collum anatomicum, and an inserted guide rod.

0. The user provides a desired distance between the entry point and the collum anatomicum (e.g., 0 mm, or 5 mm medial).
1. The user acquires an axial X-ray image of the proximal part of the humerus as depicted in FIG. 7.
2. The system detects the outline of the humeral head (e.g., with a neural network). Based on the detected outline, the system approximates the humeral head by a circle (labeled HH), i.e., it estimates 2D center and radius. This may include multiple candidates for the humeral head (2D center and radius), which are ranked based on their plausibility (e.g., based on a statistical model, mean-squared approximation error, confidence level, etc.). Based on the detected shaft axis (labeled IC), the system rotates the image such that the shaft axis is a vertical line. The system evaluates whether the center of the head is close enough to the shaft axis. If the distance between the center of the head and the shaft axis is too large, the system advises the user to apply traction force on the arm in distal direction in order to correct the translational reposition (i.e., head vs. shaft; forces by the soft tissue will lead to a reposition perpendicular to the traction force).
3. The system estimates an initial entry point (labeled EP), which lies somewhere between the intersection points of the humeral head and the shaft axis (e.g., 20% above the center of the intersection points).
4. The user places a guide rod onto the initial guess of the entry point from step 3.
5. The user acquires a further axial X-ray image, where the guide rod (labeled OI) is visible as depicted in FIG. 8.
6. The system detects the humeral head (labeled HH) (2D center and radius) and the 2D shaft axis (labeled IC) and localizes the guide rod (labeled OI) in order to obtain the 2D coordinates of its tip and the 2D scaling (based on the known diameter of the guide rod).
7. The system advises the user to rotate the C-arm around its C axis (further allowed C-arm movements are translations in distal-proximal or anterior-posterior direction; prohibited movements are other rotations and a translation in medial-lateral direction).
8. The user acquires an AP X-ray image (which does not need to be a true AP image) of the proximal part of the humerus as depicted in FIG. 9 while not moving the tip of the guide rod (angular movements of the guide rod are allowed as long as the tip stays in place).
9. The system detects the humeral head (labeled HH) (2D center and radius) and the 2D shaft axis (labeled IC) and localizes the guide rod (labeled OI) in order to obtain the 2D coordinates of its tip and the 2D scaling (based on the known diameter of the guide rod).
10. Based on the information from steps 6 to 9, the system performs an image registration as depicted in FIG. 10 and calculates the spherical approximation of the humeral head (labeled HH3D) and the 3D shaft axis, which lies in the same coordinate system as the sphere.
11. There are four points (i.e., two per image, axial and AP) (labeled CA in FIG. 11 and FIG. 12) that define the start and the end of the circular part of the projected humeral head. The system detects at least three out of these four points. Based on these at least three points, the system determines the collum anatomicum in 3D (e.g., by defining a plane based on the three points, which intersects with the spherical approximation of the humeral head).
12. The system may use the fourth point from step 11 as well in order to improve determining the collum anatomicum (e.g., with a weighted least squares, where the weights are based on the individual confidence level of each of the four points).
13. When the anatomy is rotated virtually in space such that the 3D shaft axis is a vertical line and the humeral head is above the shaft, the entry point is defined as the highest point in space on the collum anatomicum (labeled CA3D in FIG. 13). Based on the setting from step 0 and the results from steps 10 to 12, the system calculates the final entry point (labeled EP).
14. The user places the guide rod on the calculated entry point and acquires a new AP X-ray image as depicted in FIG. 14.
15. The system detects the tip of the guide rod (labeled OI) and evaluates whether the tip of the guide rod is located close enough to the calculated entry point (labeled EP).
16. Steps 14 and 15 are repeated until the tip of the guide rod is close enough to the entry point.
17. Optional instruction for the angular movement of the guide rod.
    a. Based on the latest image registration (which includes the humeral head in 3D), the system determines the spatial relation between the humeral head and the guide rod as depicted in FIG. 15 and FIG. 16. If the direction of the guide rod deviates too much from the optimal insertion direction, the system gives an instruction for the angular movement of the guide rod. The optimal insertion direction may be estimated, e.g., with statistical models, or by comparing the axis of the guide rod (labeled OIA) with the humeral head axis (labeled HA).
    b. If an instruction was given in step a, the user follows the instruction and acquires a new X-ray image from the same direction. An image difference analysis detects changes in the image and updates the image registration.
    c. Steps a and b are repeated until no further angular movement of the guide rod is needed.
18. Optional improvement of the image registration and validation of the humeral head outline.
    a. The user inserts the guide rod as depicted in FIG. 17.
    b. The user acquires an X-ray image (e.g., axial as depicted in FIG. 18).
    c. The system localizes the guide rod (labeled OI) and detects the humeral head (labeled HH) (2D center and radius).
    d. The system advises the user to rotate the C-arm around its C axis (see step 7 for additional possible C-arm movements).
    e. The user acquires an X-ray image from the other direction (e.g., AP as depicted in FIG. 19) without moving the guide rod.
    f. The system localizes the guide rod (labeled OI) and detects the humeral head (labeled HH) (2D center and radius).
    g. Based on the information from both images, the system performs an image registration. Since a 3D model of the guide rod is known, the image registration is more accurate than in step 10.

h. Based on the image registration, the system may validate the detection of the humeral head in both images.

i. Based on the validation result, the system optimizes the outline of the humeral head in both images (e.g., by choosing another candidate for the humeral head).

19. Optional correction of the rotational dislocation of the humeral head.

a. The user acquires an X-ray image (axial or AP). The system localizes the guide rod and detects the 2D shaft axis as well as the 2D humeral head axis (defined by the visible circular part of the humeral head).

b. If the previous image had a significantly different imaging direction (e.g., axial in the previous image and AP in the current image), the system performs an image registration based on the latest image pair. Based on the image registration, the system determines the ideal 2D angle between the shaft axis and the head axis for the current image.

c. If the previous image had a very similar imaging direction (identified by, e.g., an image difference analysis), the ideal 2D angle between the shaft axis and the head axis remains unchanged (compared to the previous image).

d. The system calculates the current 2D angle between the shaft axis and the head axis.

e. If the angle between the shaft axis and the head axis is not close enough to the ideal angle from step 19b or 19c (e.g., 20° in an axial image, or 130° in an AP image), the system gives an instruction in order to correct the rotational dislocation in dorsal-ventral (axial image) or medial-lateral (AP image) direction.

f. If the previous image had a very similar imaging direction, but the visible circular part of the humeral head is smaller or larger compared to the previous image (e.g., due to a prior correction of the dislocation), the system gives an additional instruction to rotate the C-arm around its C-axis in order to change the imaging direction for the next image (i.e., to update the image registration) because the rotational dislocation may have changed also for the other imaging direction.

g. If an instruction was given, the user corrects the rotational dislocation (and rotates the C-arm if needed) and returns to step 19a.

20. Optional torsion check.

a. The user places the forearm such that it is parallel to the body (or upper leg).

b. The user acquires an axial X-ray image.

c. The system detects the humeral head axis and the 2D center of the glenoid. The system calculates the distance between the center of the glenoid and the head axis. Based on this result, the system gives an instruction in which direction and by which angle the torsion needs to be corrected.

d. The user corrects the torsion by rotating the head in the direction and by the angle from step c.

e. Steps 20b to 20d are repeated until the center of the glenoid is close enough to the humeral head axis.

Potential modification: Instead of estimating the entry point in step 3 at 20% above (medial to) the center of the intersection points, the system may use a higher value (e.g., 70%) to ensure that the tip of the guide rod is located on the spherical part of the humeral head. In step 10, the system may use the information that the tip of the guide rod is located on the spherical approximation of the humeral head to improve the image registration. Due to the 70%-method above, the current position of the tip of the guide rod has a larger distance to the entry point (compared to the 20%-method). When guiding the user to reach the entry point with the tip of the guide rod (steps 14 to 16), the system determines whether the viewing direction has changed (e.g., by an image difference analysis). If the viewing direction has not changed, the calculated entry point is used from the previous X-ray image and the guidance information is updated based on the updated detected position of the tip. If the viewing direction has changed only slightly, the entry point is shifted accordingly (e.g., by a technique called object tracking, see, e.g., S. R. Balaji et al., "A survey on moving object tracking using image processing" (2017)). If the viewing direction has changed significantly, the system instructs the user to rotate the C-arm around its C-axis and to acquire an X-ray image from a different viewing direction (e.g., axial if the current image was AP) while not moving the tip of the guide rod. Based on the updated images, the system performs an image registration based on the information acquired by the previous registration (e.g., the radius of the ball approximation of the humeral head), displays the entry point in the current image and navigates the user to reach the entry point with the tip of the guide rod.

Determining the Angle of Anteversion of a Femur

Figure 34:
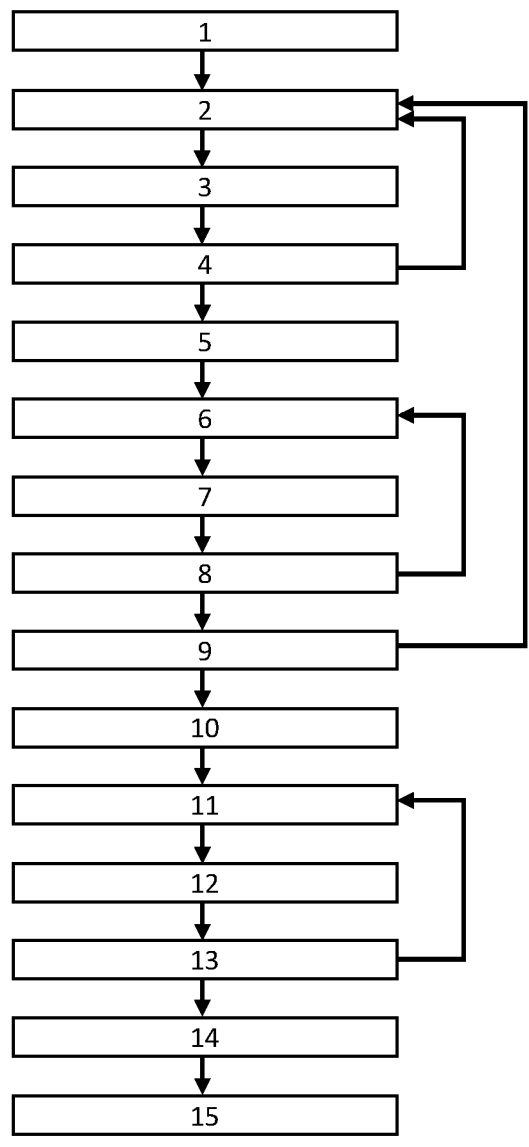
FIG. 34 shows a potential workflow for determining the angle of anteversion of a femur.

In the following, an example workflow is presented that determines the AV angle either before or after inserting an implant, and which may be more robust and/or more precise than the state of the art. According to an embodiment, the entire procedure for determining the angle of anteversion of a femur may proceed as follows (cf. FIG. 34).

1. The user places the tip of an opening instrument approximately onto the tip of the greater trochanter.

Figure 20:
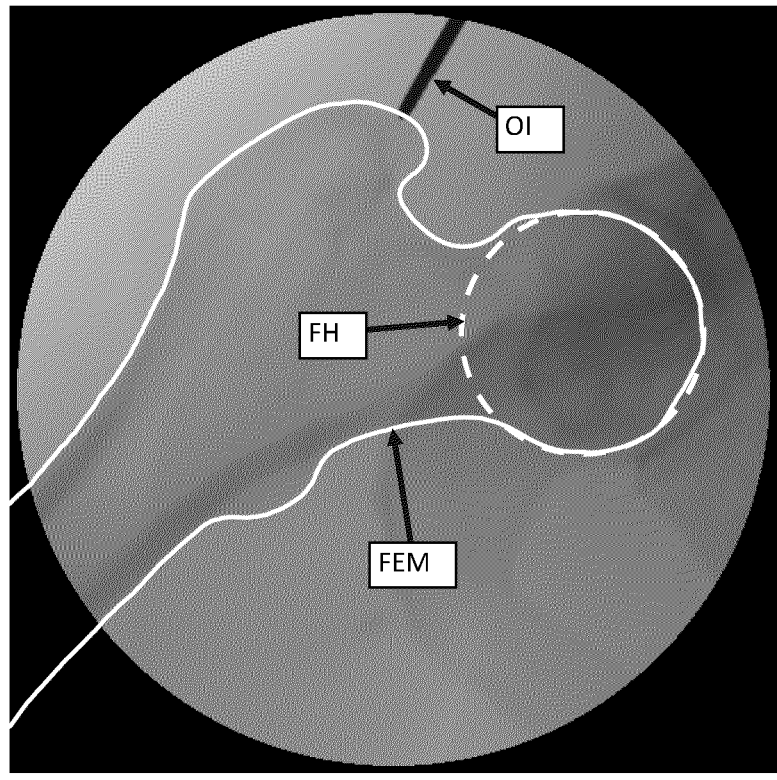
FIG. 20 shows an AP X-ray image of the proximal part of a femur, its outline, and an opening instrument.

2. The user acquires an AP X-ray image of the proximal part of the femur as depicted in FIG. 20.

3. The system detects the 2D outline of the femur (labeled FEM) and the femoral head, which is approximated by a circle (labeled FH) (i.e., it is determined by 2D center and 2D radius) and localizes the tip of the opening instrument (labeled OI).

4. If some important parts of the femur or the tip of the opening instrument are not sufficiently visible, the system gives an instruction to rotate and/or move the C-arm, and the user returns to step 2.

5. The user rotates the C-arm around its C-axis to acquire an ML X-ray image. The user may additionally use the medial-lateral and/or the anterior-posterior shift of the C-arm. While moving the C-arm, the tip of the opening instrument must not move.

Figure 21:
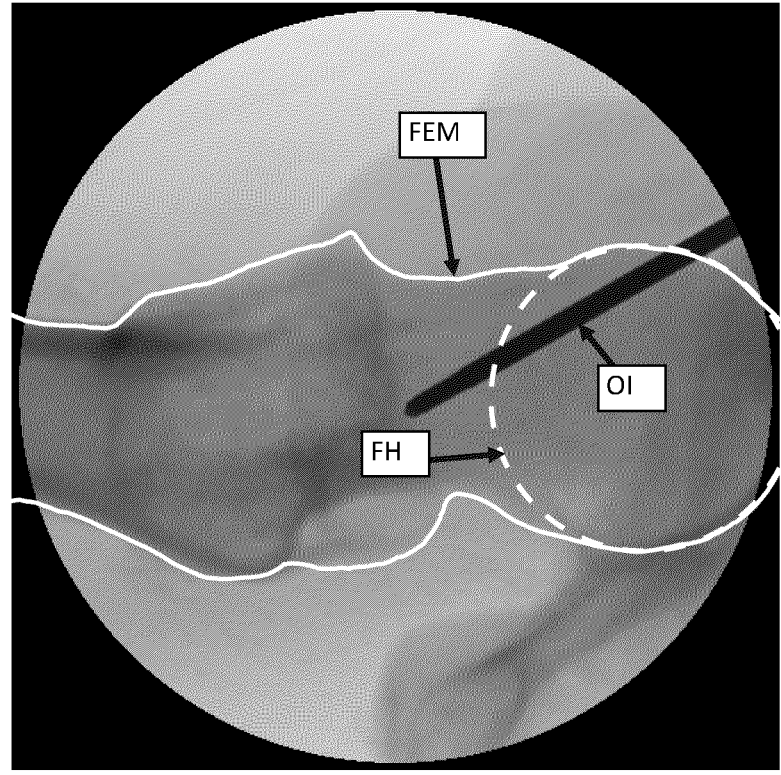
FIG. 21 shows an ML X-ray image of the proximal part of a femur, its outline, and an opening instrument.

6. The user acquires an ML X-ray image of the proximal part of the femur as depicted in FIG. 21.

7. The system detects the 2D outline of the femur (labeled FEM) and the femoral head (labeled FH) (i.e., 2D center and 2D radius) and localizes the tip of the opening instrument (labeled OI).

8. If some important parts of the femur or the tip of the opening instrument are not sufficiently visible, the system gives an instruction to move the C-arm (only translations) or to rotate the C-arm around its C-axis, and the user returns to step 6.

9. Based on the proximal AP and ML image pair, the system performs an image registration. If the image registration was not successful, the system gives an instruction to rotate and/or move the C-arm, and the user returns to step 2.

10. The user moves the C-arm in distal direction along the patient's leg. In this step, no rotational, but all three translational movements of the C-arm are allowed.

Figure 22:
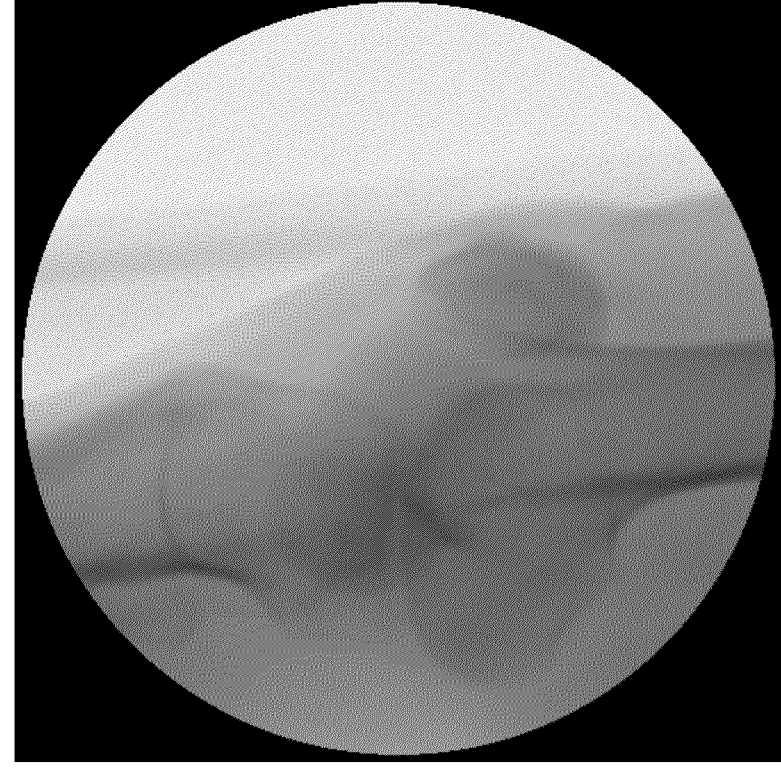
FIG. 22 shows an ML X-ray image of the distal part of a femur.
Figure 23:
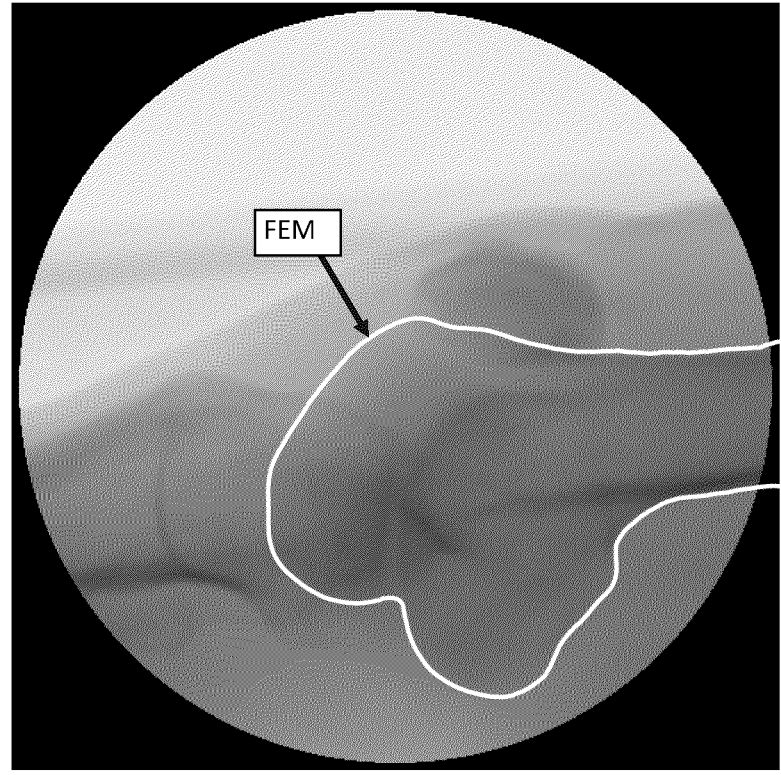
FIG. 23 shows an ML X-ray image of the distal part of a femur and its outline.

11. The user acquires an ML X-ray projection image of the distal part of the femur as depicted in FIG. 22 and FIG. 23.

12. The system detects the 2D outline of the femur (labeled FEM).

13. No particular orientation or alignment of the femoral condyles is required. If, however, some important parts of the femur are not sufficiently visible, the system gives an instruction to move the C-arm (only translations are allowed), and the user returns to step 11.

14. Based on the image registration, the system jointly fits a statistical model (which was trained on fractured and unfractured femurs) to all images such that the projected outlines of the statistical model match the detected 2D outlines of the femur in all images. This step leads directly to a 3D reconstruction of the femur. To improve the accuracy of the 3D reconstruction, the system may calculate the 3D position of the tip of the opening instrument (based on the proximal image registration) and use this point as a reference point, using the fact that the tip of the opening instrument was placed on the surface of the femur.

Figure 24:
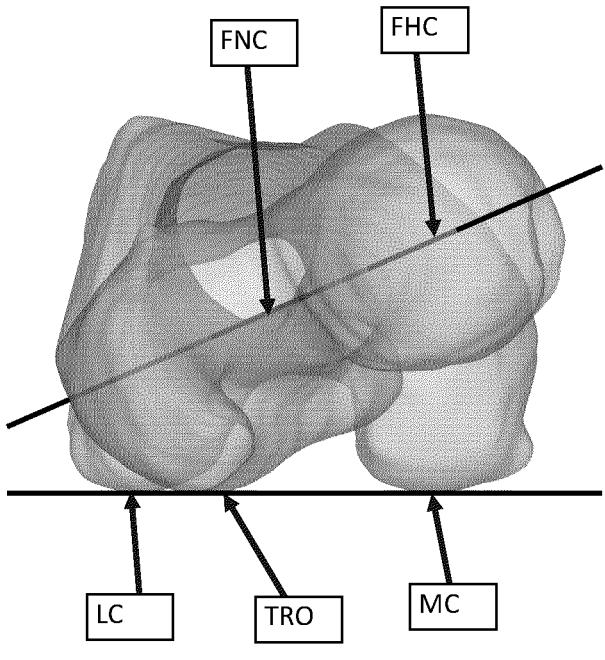
FIG. 24 shows a 3D femur and a definition of the femoral angle of anteversion.

15. The system determines the angle of anteversion based on the 3D reconstruction of the femur as depicted in FIG. 24. According to Yeon Soo Lee et al.: "3D femoral neck anteversion measurements based on the posterior femoral plane in ORTHODOC® system" (2006), the angle of anteversion may be calculated based on the center of the femoral head (labeled FHC), the center of the femoral neck (labeled FNC), the posterior apex of the trochanter (labeled TRO), and the lateral and medial apex of the posterior femoral condyles (labeled LC and MC). The system identifies these five points on the 3D reconstruction of the femur from step 10 and thus calculates the angle of anteversion.

Freehand Locking Procedure

There may be different implementations of a distal locking procedure for a femoral nail. In the following, two examples for potential workflows (one "quick" and one with "enhanced" accuracy) are presented.

Figure 35:
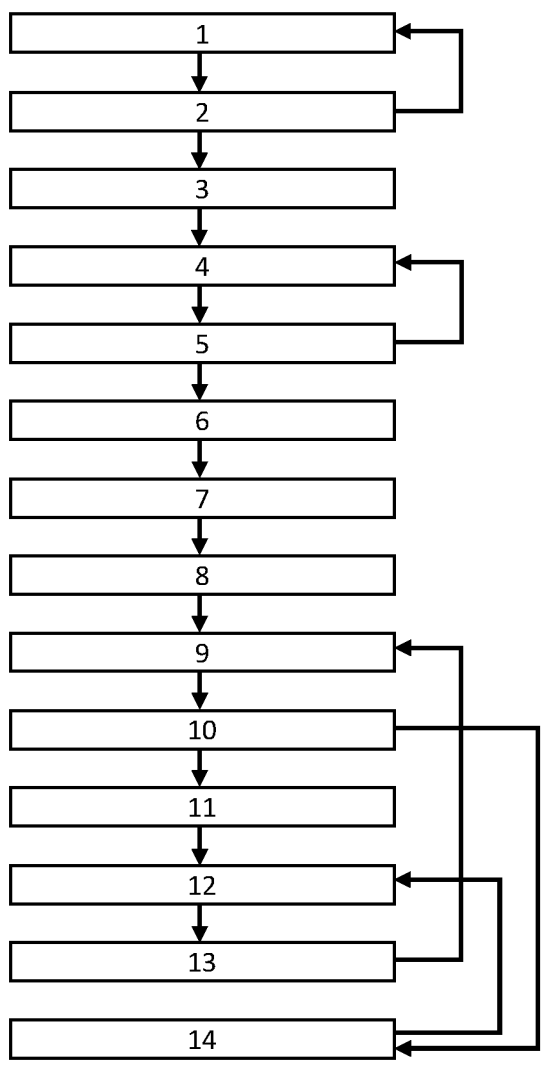
FIG. 35 shows a potential workflow for a freehand locking procedure (quick version).

Example for a Potential Workflow (Quick Version), Cf. FIG. 35

Figure 28:
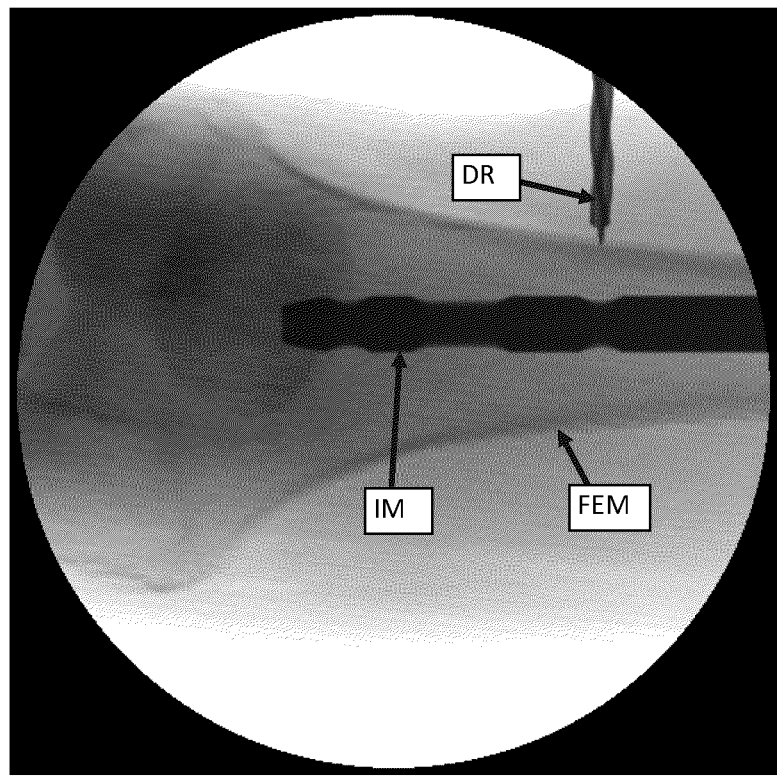
FIG. 28 shows an AP X-ray image of the distal part of a femur, an inserted implant, and a drill that was placed onto the surface of the femur.

1. The user acquires an X-ray image of the distal part of the femur (e.g., AP as depicted in FIG. 28, or ML).

2. The system localizes the implant and detects the outline of the femur. If either the implant or the outline of the femur cannot be localized, the system gives an instruction to improve visibility (e.g., by moving the C-arm). The user follows the instruction and returns to step 1.

Figure 29:
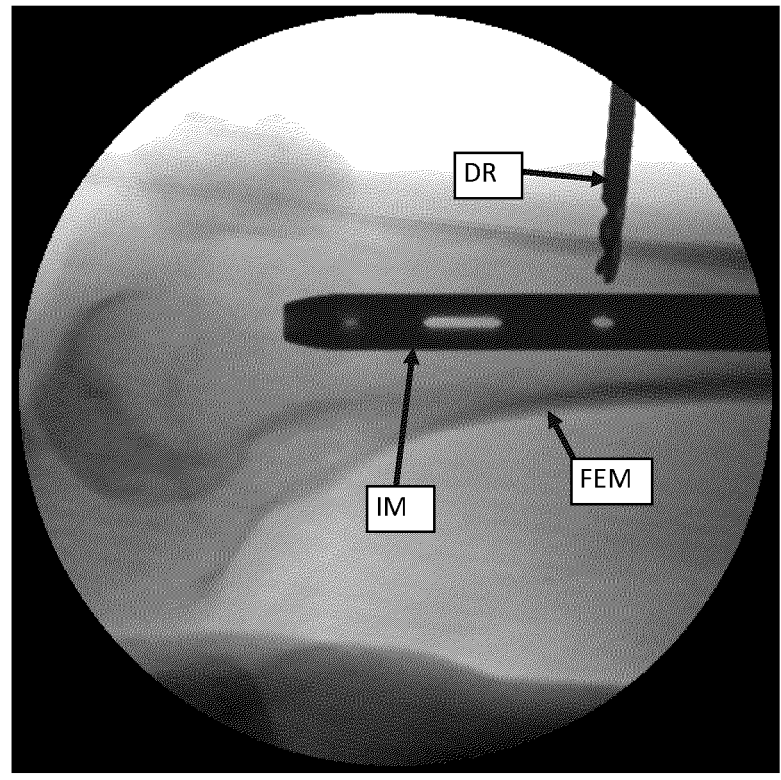
FIG. 29 shows an ML X-ray image of the distal part of a femur, an inserted implant, and a drill that was placed onto the surface of the femur.

3. The user places a drill onto the surface of the femur (e.g., at the nail hole trajectory). The user acquires an X-ray image from another viewing direction (e.g., 25°-ML as depicted in FIG. 29).

4. The system localizes the implant (labeled IM), detects the outline of the femur (labeled FEM), and localizes the drill (labeled DR).

5. If the drill tip cannot be localized, the system gives an instruction to improve visibility of the drill tip (e.g., by moving the C-arm). The user follows the instruction, acquires a new image, and returns to step 4.

Figure 30:
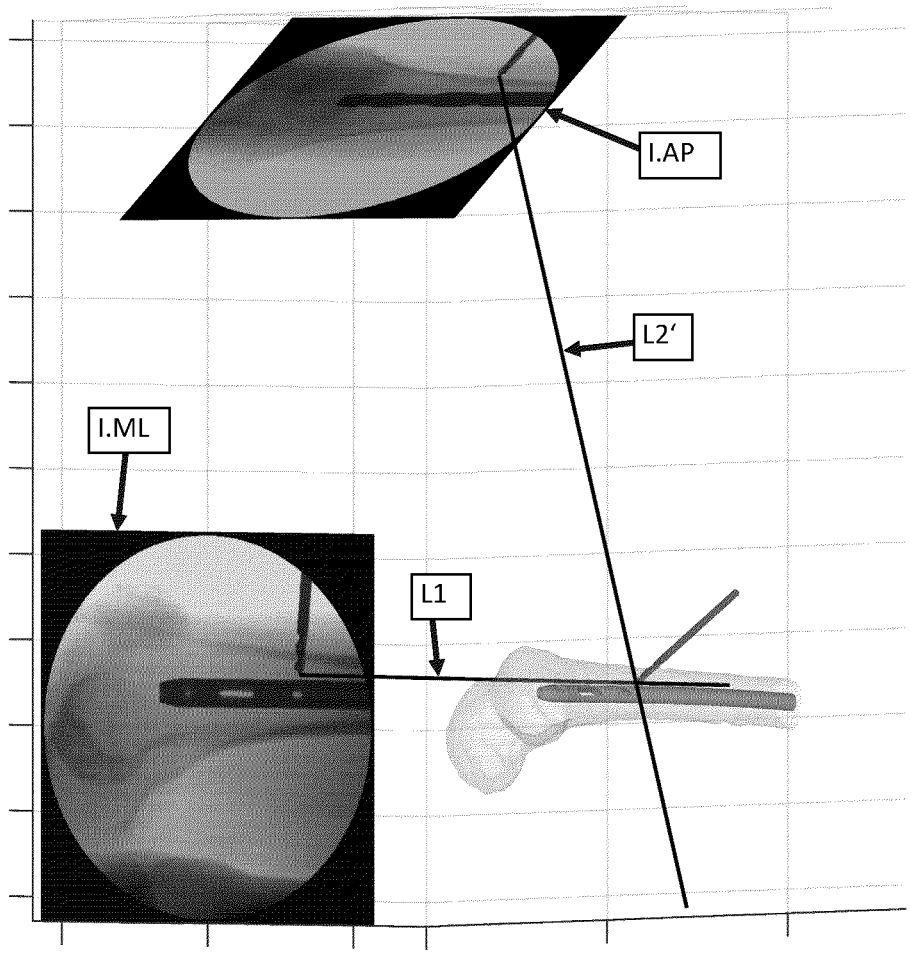
FIG. 30 shows an image registration for the distal part of a femur based on an AP and an ML X-ray image. It includes a femur, an inserted implant, and a drill.
Figure 31:
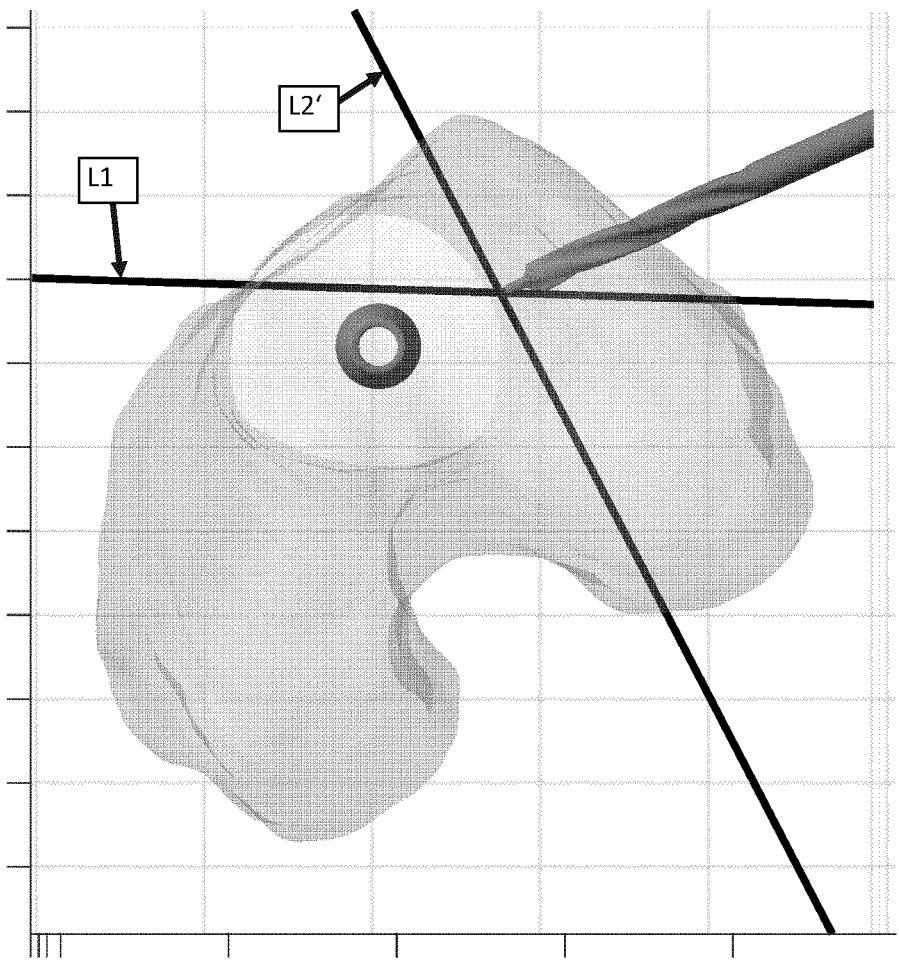
FIG. 31 shows the same constellation as FIG. 30 from a different viewing direction.

6. Based on the localization of the implant in both images (labeled I.AP and I.ML in FIG. 30), the system performs an image registration as depicted in FIG. 30 and FIG. 31.

7. Based on the image registration from step 6, the system fits a statistical model of the femur by matching its projected outlines to the detected outlines of the femur in both images (i.e., it determines the rotation and translation of the femur in both images, the scaling, and the modes of the statistical model).

8. For the current image, the system defines a line from the drill tip in the image plane to the focal point. This line intersects twice with the reconstructed femur (i.e., entry and exit point). The point that is closer to the focal point is chosen as the current 3D position of the drill tip. The system may calculate the locking screw length based on the shaft diameter of the reconstructed femur along the nail hole trajectory.

9. Based on the known spatial relation between the femur and the implant (due to the image registration and the reconstruction of the femur), the system calculates the spatial relation between the drill and the implant.

10. If the drill trajectory goes through the nail hole, the system gives an instruction to start drilling, the user starts drilling, and the user goes to step 14.

11. If the drill trajectory does not go through the nail hole, the system gives an instruction for moving the drill tip and/or rotating the drill. The user follows the instruction and acquires a new X-ray image.

12. The system evaluates whether the viewing direction has changed (e.g., by an image difference analysis). If the viewing direction has not changed, the system may use most results from the previous image, but it localizes the drill. If the viewing direction or any other relevant image content (e.g., by image blurring effects, occlusion, etc.) has changed, the system may use this information to improve the image registration (e.g., by using the additional viewing direction of the current image). The system localizes the implant and the drill, detects the outline of the femur, and fits the reconstructed femur into the current image.

13. The user returns to step 9.

Figure 32:
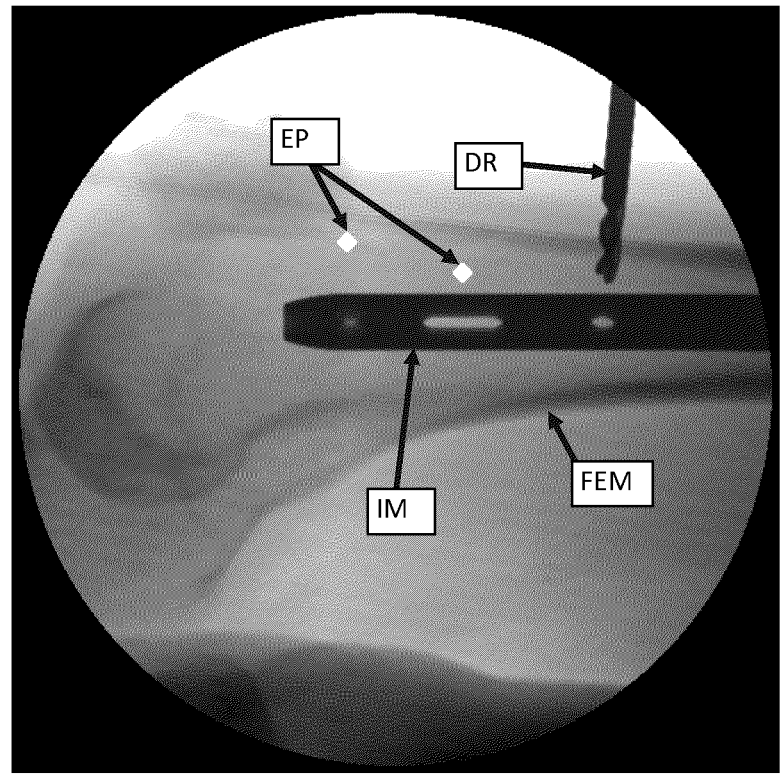
FIG. 32 shows an ML X-ray image of the distal part of a femur with calculated entry points for multiple nail holes.

14. If the user wants to lock further holes, the system displays the entry points for all nail holes (given by the intersection of the 3D reconstruction of the femur with the implantation curve for an ideal locking position) and gives an instruction how to move the drill tip in order to reach the entry point. An example is depicted in FIG. 32. The user places the drill tip onto the calculated entry point (labeled EP) and returns to step 12.

Figure 36:
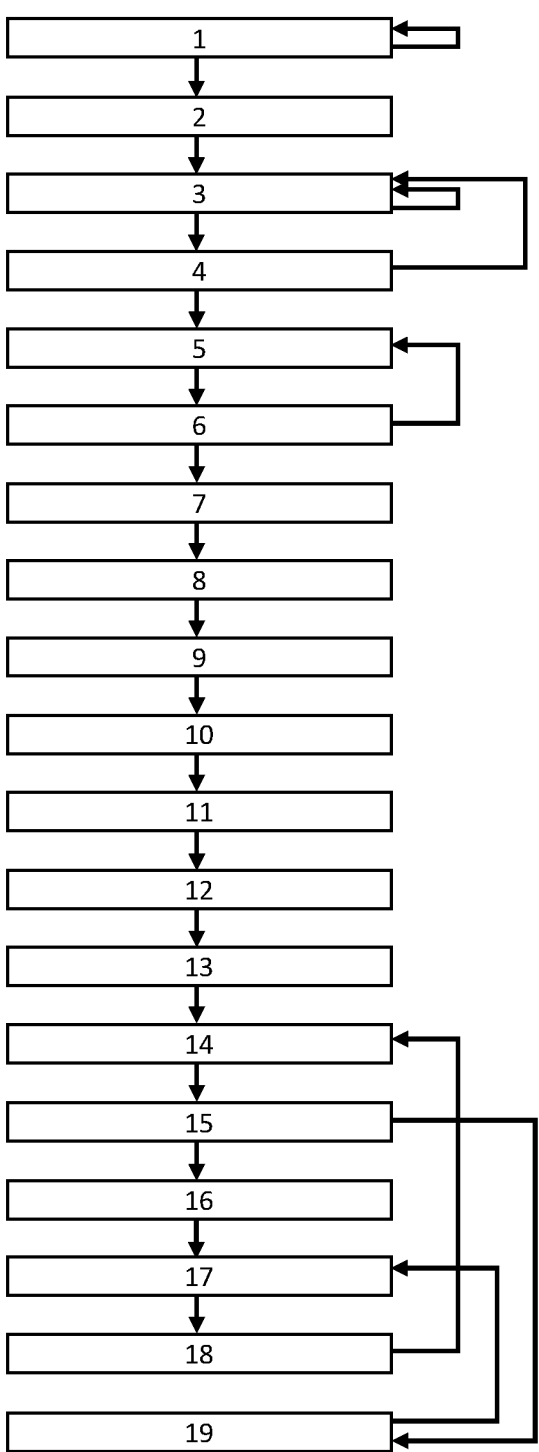
FIG. 36 shows a potential workflow for a freehand locking procedure (enhanced version).

Example for a Potential Workflow (Enhanced Version), Cf. FIG. 36

1. Optional: The user acquires an X-ray image of the distal part of the femur (e.g., AP as depicted in FIG. 28, or ML). The system localizes the implant (labeled IM) and detects the outline of the femur (labeled FEM). If either the implant or the outline of the femur cannot be localized, the system gives an instruction to improve the visibility (e.g., by moving the C-arm). The user follows the instruction and returns to the beginning of this step.

2. The user places a drill onto the surface of the femur (e.g., onto the nail hole trajectory).

3. The user acquires an X-ray image of the distal part of the femur (e.g., ML or AP). The system localizes the implant (labeled IM), detects the outline of the femur (labeled FEM), and localizes the drill (labeled DR). If either the implant or the outline of the femur or the drill tip cannot be localized, the system gives an instruction to improve the visibility (e.g., by moving the C-arm). The user follows the instruction and returns to the beginning of this step. Based on the 3D reconstruction of the bone relative to the coordinate system of the nail, the system computes the needed length of sub implants (e.g., locking screws) and displays according information.

4. The user acquires an X-ray image from another viewing direction (e.g., 25°-ML as depicted in FIG. 29). The drill tip must not move between the images. If it had moved, the system may be able to detect this and would request the user to go back to step 3.

5. The system localizes the implant (labeled IM), detects the outline of the femur (labeled FEM), and localizes the drill (labeled DR).

6. If the drill tip cannot be localized, the system gives an instruction to improve the visibility of the drill tip (e.g., by moving the C-arm). The user follows the instruction, acquires a new image, and returns to step 5.

7. Based on the localization of the implant in at least two images (labeled LAP and I.ML in FIG. 30), the system performs an image registration as depicted in FIG. 30 and FIG. 31.

8. Based on the image registration from step 7, but possibly also using information from previous image registrations the system fits a statistical model of the femur by matching its projected outlines to the detected outlines of the femur in the images (i.e., it determines the rotation and translation of the femur in both images, the scaling, and the modes of the statistical model). Optional: The system may update the calculated sub-implant length based on the reconstructed bone and the determined nail hole trajectories.

9. For the current image, the system defines a line L1 (labeled L1 in FIG. 31) from the drill tip in the image plane to the focal point. L1 intersects twice with the reconstructed femur (i.e., entry and exit point). The point that is closer to the focal point is chosen as an initial value for the current 3D position of the drill tip.

10. For the image from the other viewing direction containing the drill tip, the system defines a line L2 from the drill tip in the image plane to the focal point (i.e., in the corresponding coordinate system of that image). Based on the image registration, this line is transformed into the coordinate system of the current image. The transformed line is called L2' (labeled L2' in FIG. 31).

11. If the smallest distance between L1 and L2' is higher than a certain threshold, the system may advise the user to return to step 4 because most likely the drill tip has moved between the images. Optional: If the user ensures that the drill tip has not moved between the generation of the image pair that was used for the image registration, the system improves the image registration by optimizing the localization of the implant in both images and minimizing the distance between L1 and L2'. (If the localization of the implant and the drill tip is perfect in both images and the drill tip was not moved between the images, L1 and L2' will intersect.)

12. The point on L1 that has the smallest distance to L2' is chosen as a further initial value for the current 3D position of the drill tip.

13. Based on the two solutions for the 3D position of the drill tip (i.e., from steps 9 and 12), the system finds the current 3D position of the drill tip (e.g., by choosing the solution from step 12, or by averaging both solutions). Since the drill tip is on the surface of the femur, the system improves the 3D reconstruction of the femur under the constraint that the estimated 3D position of the drill tip is on the surface of the reconstructed femur. The system may validate the previously calculated sub-implant lengths based on the improved reconstruction of the femur. If the updated lengths deviate from the previously calculated screw lengths (possibly considering the available length increments of the sub implants), the system notifies the user.

14. Based on the known spatial relation between the femur and the implant (due to the image registration and the reconstruction of the femur), the system calculates the spatial relation between the drill and the implant.

15. If the drill trajectory goes through the nail hole, the system gives an instruction to start drilling, the user starts drilling and inserts the sub implant after drilling, then goes to step 19.

16. If the drill trajectory does not go through the nail hole, the system gives an instruction for moving the drill tip and/or rotating the drill. The user follows the instruction and acquires a new X-ray image.

17. The system evaluates whether the viewing direction has changed (e.g., by an image difference analysis). If the viewing direction has not changed, the system may use most results from the previous image, but it localizes the drill. If the viewing direction or any other relevant image content (e.g., by image blurring effects, occlusion, etc.) has changed, the system may use this information to improve the image registration (e.g., by using the additional viewing direction of the current image). The system localizes the implant, if available optimized by the localization of the already inserted sub-implants by taken into account the available information about their entry points, and the drill, detects the outline of the femur, and fits the reconstructed femur into the current image.

18. The user returns to step 14.

19. If the user wants to lock further holes, the system displays the entry points for all nail holes (given by the intersection of the 3D reconstruction of the femur with the implantation curve for an ideal locking position) and gives an instruction how to move the drill tip in order to reach the entry point. An example is depicted in FIG. 32. The user places the drill tip onto the calculated entry point (labeled EP) and returns to step 17.

If at any time, the user decides to check whether the locking of a hole has been successful, he may acquire an image with an imaging direction deviating less than 8 degree from the locking hole trajectory and the system would automatically evaluate, whether the locking has been successful or not. In case the last hole has been locked, or in case the system has information that would require a validation of the performed locking procedure, the system may guide the user to reach above C-arm position relative to the locking hole trajectory.

To support performing a skin incision at the right spot for positioning a drill on the proposed entry point, the system may project the skin entry point based on the implantation curve and the entry point on the bone by estimating the distance between the skin and the bone.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the invention as set forth in the appended claims and their legal equivalents.

The invention claimed is:

1. A system for processing X-ray images, the system comprising a processing unit being configured to receive a lateral 2D X-ray image showing a femur, determine a first point associated with one of a plurality of structures of interest, determine an implantation curve within the femur for an implant intended to be implanted, wherein the implantation curve has a predetermined relation to the first point and wherein an entry point for an insertion of the implant into the femur is located on the implantation curve, wherein the predetermined relation between the implantation curve and the first point fulfills a first one of the conditions out of the group consisting of:

(i) when the structure of interest is a femur head, the first point is associated with a centre of the femur head and is located on a proximal extension of the implantation curve, (ii) when the structure of interest is a narrow portion of a femur neck, the first point is associated with a centre of a cross section of the narrow portion of the femur neck and a proximal extension of the implantation curve is in said narrow portion closer to the first point then to a surface of the femur neck, (iii) when the structure of interest is a narrow portion of a femur shaft, the first point is associated with a centre of a cross section of the narrow portion of the femur shaft and the implantation curve is in said narrow portion closer to the first point then to a surface of the femur shaft, (iv) when the structure of interest is an isthmus of a femur, the first point is associated with a centre of a cross section of the isthmus and the first point is located on the implantation curve, (v) when the structure of interest is a hole in the implant, the hole having a hole axis, the first point is associated with a centre of the hole and the implantation curve is parallel to the hole axis, wherein the processing unit is further configured to determine at least one further point associated with another one of the plurality of structures of interest, wherein the predetermined relation between the implantation curve and one of the at least one further point fulfills a further one of the conditions, respectively.

2. The system of claim 1, wherein in case of the femur head the center of the femur head is outside of the imaged area of the X-ray image and/or wherein in case of the isthmus of a femur the center of a cross section of the isthmus is outside the imaged area of the X-ray image.

3. The system of claim 1, wherein 20 percent to 80 percent of the structure of interest is visible in the 2D X-ray image.

4. The system of claim 1, wherein the determination of the implantation curve is based on a geometry of the implant intended to be implanted.

5. The system of claim 1, wherein the processing unit is further configured to receive a further 2D X-ray image showing the femur, and to register the 2D X-ray image and the further 2D X-ray image.

6. The system of claim 5, wherein the processing unit is further configured to determine a 3D reconstruction of at least an area of a surface of the femur.

7. The system of claim 6, wherein the processing unit is further configured to determine the entry point on the basis of a determination of an intersection of the implantation curve and the area of the surface of the femur.

8. The system of claim 1, wherein the processing unit is further configured to provide an indication if one of the conditions is not fulfilled.

9. The system of claim 8, wherein the processing unit is further configured to provide information as to how an imaging device should be adjusted for a new 2D X-ray image.

10. The system of claim 1, wherein the processing unit is further configured to determine the entry point on the basis of detection of at least a point of an instrument, the instrument being in contact with the surface of the femur.

11. The system of claim 1, wherein the processing unit is further configured to determine the entry point on the basis of detecting a contact point of an instrument on a trochanter rim.

12. The system of claim 1, wherein the processing unit is further configured to determine the entry point on the basis of detecting a contact point of an instrument on a *piriformis* fossa.

13. The system of claim 1, wherein the processing unit is further configured to determine the entry point on the basis of determination of intersection of the implantation curve and an area of the surface of the femur.

14. The system of claim 1, wherein the processing unit is further configured to determine the entry point on the basis of a determination of reposition of bone fragments.

* * * * *